(12) United States Patent
Domon et al.

(10) Patent No.: US 8,835,097 B2
(45) Date of Patent: *Sep. 16, 2014

(54) SULFONIUM SALT, POLYMER, CHEMICALLY AMPLIFIED RESIST COMPOSITION USING SAID POLYMER, AND RESIST PATTERNING PROCESS

(75) Inventors: Daisuke Domon, Jyoetsu (JP); Keiichi Masunaga, Jyoetsu (JP); Satoshi Watanabe, Jyoetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 12 days.

This patent is subject to a terminal disclaimer.

(21) Appl. No.: 13/476,629

(22) Filed: May 21, 2012

(65) Prior Publication Data

US 2012/0308920 A1 Dec. 6, 2012

(30) Foreign Application Priority Data

May 30, 2011 (JP) ................... 2011-120454

(51) Int. Cl.
| | | |
|---|---|---|
| G03F 7/004 | (2006.01) | |
| C07C 309/12 | (2006.01) | |
| C07C 309/19 | (2006.01) | |
| C07C 309/22 | (2006.01) | |
| C08F 20/28 | (2006.01) | |
| G03F 7/039 | (2006.01) | |
| C08F 220/38 | (2006.01) | |

(52) U.S. Cl.
CPC ............ G03F 7/0392 (2013.01); C07C 309/12 (2013.01); C08F 20/28 (2013.01); C07C 309/19 (2013.01); C07C 309/22 (2013.01); G03F 7/0045 (2013.01); G03F 7/0397 (2013.01); C08F 2220/382 (2013.01); Y10S 430/111 (2013.01); Y10S 430/122 (2013.01); Y10S 430/123 (2013.01)
USPC ........ 430/270.1; 430/910; 430/921; 430/922; 526/266; 526/268; 549/300; 562/52; 562/100; 562/109; 562/110

(58) Field of Classification Search
CPC ... G03F 7/0045; G03F 7/0397; C07C 309/12; C07C 309/19; C07C 309/22; C08F 20/28
USPC ............. 549/300; 526/268, 266; 562/52, 100, 562/109, 110
See application file for complete search history.

(56) References Cited

U.S. PATENT DOCUMENTS

| | | | |
|---|---|---|---|
| 5,650,483 A | 7/1997 | Malik et al. | |
| 5,945,250 A | 8/1999 | Aoai et al. | |
| 6,048,672 A | 4/2000 | Cameron et al. | |
| 6,280,898 B1 | 8/2001 | Hasegawa et al. | |
| 7,833,694 B2 | 11/2010 | Hasegawa et al. | |
| 8,062,831 B2 | 11/2011 | Shinachi et al. | |
| 2002/0102491 A1 | 8/2002 | Kodama et al. | |
| 2003/0013039 A1 | 1/2003 | Kobayashi et al. | |
| 2004/0197697 A1 | 10/2004 | Korionoff et al. | |
| 2004/0260031 A1 | 12/2004 | Takeda et al. | |
| 2006/0228648 A1 | 10/2006 | Ohsawa et al. | |
| 2007/0078269 A1 | 4/2007 | Harada et al. | |
| 2007/0148594 A1 | 6/2007 | Funatsu et al. | |
| 2007/0149702 A1 | 6/2007 | Ando et al. | |
| 2007/0160929 A1 | 7/2007 | Hasegawa et al. | |
| 2007/0264596 A1 | 11/2007 | Ohsawa et al. | |
| 2008/0026331 A1 | 1/2008 | Hasegawa et al. | |
| 2008/0085469 A1 | 4/2008 | Ohsawa et al. | |
| 2008/0096128 A1 | 4/2008 | Takeda et al. | |
| 2008/0102407 A1 | 5/2008 | Ohsawa et al. | |
| 2008/0118860 A1 | 5/2008 | Harada et al. | |
| 2008/0305411 A1 | 12/2008 | Koitabashi et al. | |
| 2009/0069521 A1 | 3/2009 | Nagai et al. | |
| 2009/0233223 A1 | 9/2009 | Tachibana et al. | |

(Continued)

FOREIGN PATENT DOCUMENTS

| | | |
|---|---|---|
| CA | 2049772 A1 | 2/1992 |
| JP | A-3-501970 | 5/1991 |
| JP | A-04-230645 | 8/1992 |
| JP | A-09-325497 | 12/1997 |
| JP | A-11-282168 | 10/1999 |

(Continued)

OTHER PUBLICATIONS

Jul. 17, 2012 Notification of Reasons for Refusal issued in Japanese Application No. 2010-021078 (with partial translation).
Devoe et al., "Photochemistry and Photophysics of Onium Salts*," *Advances in Photochemistry*, vol. 17, pp. 313-355, 1992, John Wiley & Sons.

(Continued)

*Primary Examiner* — John Chu
(74) *Attorney, Agent, or Firm* — Oliff, PLC

(57) ABSTRACT

There is disclosed a sulfonium salt shown by the following general formula (1). There can be a sulfonium salt capable of introducing an acid-generating unit generating an acid having an appropriate acid strength and not impairing adhesion with a substrate into a base polymer; a polymer using the said sulfonium salt; a chemically amplified resist composition using the said polymer as a base polymer; and a patterning process using the said chemically amplified resist composition.

28 Claims, No Drawings

(1)

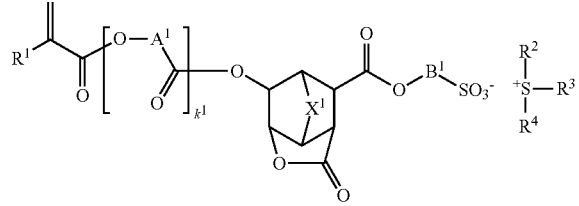

(56) References Cited

U.S. PATENT DOCUMENTS

| | | |
|---|---|---|
| 2009/0274984 A1 | 11/2009 | Shinachi et al. |
| 2009/0318652 A1 | 12/2009 | Nagai et al. |
| 2010/0075256 A1 | 3/2010 | Joo et al. |
| 2010/0099042 A1 | 4/2010 | Ohashi et al. |
| 2010/0136478 A1 | 6/2010 | Kawaue et al. |
| 2010/0248149 A1 | 9/2010 | Tsuchimura et al. |
| 2010/0297560 A1 | 11/2010 | Seshimo et al. |
| 2010/0304294 A1 | 12/2010 | Ichikawa et al. |
| 2011/0189607 A1* | 8/2011 | Ohashi et al. ............ 430/270.1 |
| 2012/0308932 A1 | 12/2012 | Sagehashi et al. |

FOREIGN PATENT DOCUMENTS

| | | |
|---|---|---|
| JP | A-2000-159758 | 6/2000 |
| JP | A-2002-214774 | 7/2002 |
| JP | A-2003-066612 | 3/2003 |
| JP | A-2004-002252 | 1/2004 |
| JP | A-2004-115630 | 4/2004 |
| JP | A-2004-531749 | 10/2004 |
| JP | B2-3613491 | 11/2004 |
| JP | A-2005-008766 | 1/2005 |
| JP | A-2005-084365 | 3/2005 |
| JP | A-2006-178317 | 7/2006 |
| JP | A-2006-306856 | 11/2006 |
| JP | A-2007-145797 | 6/2007 |
| JP | A-2007-182488 | 7/2007 |
| JP | A-2007-197718 | 8/2007 |
| JP | A-2007-304490 | 11/2007 |
| JP | A-2008-031298 | 2/2008 |
| JP | A-2008-080474 | 4/2008 |
| JP | A-2008-102383 | 5/2008 |
| JP | A-2008-106045 | 5/2008 |
| JP | A-2008-111103 | 5/2008 |
| JP | A-2008-133448 | 6/2008 |
| JP | A-2008-304590 | 12/2008 |
| JP | A-2009-007323 | 1/2009 |
| JP | A-2009-242789 | 10/2009 |
| JP | B2-4539865 | 9/2010 |
| JP | A-2010-250290 | 11/2010 |
| JP | A-2010-271501 | 12/2010 |
| JP | A-2011-006398 | 1/2011 |
| JP | A-2011-026300 | 2/2011 |
| JP | A-2011-037836 | 2/2011 |
| JP | A-2011-085878 | 4/2011 |
| WO | WO 89/03389 | 4/1989 |
| WO | WO 2006/121096 A1 | 11/2006 |
| WO | WO 2007/069640 A1 | 6/2007 |

OTHER PUBLICATIONS

Arimitsu et al., "Sensitivity Enhancement of Chemical-Amplification-Type Photoimaging Materials by Acetoacetic Acid Derivatives," *Journal of Photopolymer Science and Technology*, vol. 8, No. 1, pp. 43-46, 1995.

Arimitsu et al., "Effect of Phenolic Hydroxyl Residues on the Improvement of Acid- Proliferation-Type Photoimaging Materials," *Journal of Photopolymer Science and Technology*, vol. 9, No. 1, pp. 29-30, 1996.

Lowe, "Synthesis of sulphonium salts," *The Chemistry of the Sulphonium Group*, Ed. Stirling et al., Chapter 11, pp. 267-312, 1981, John Wiley & Sons Ltd.

Mar. 1, 2013 Office Action issued in U.S. Appl. No. 13/013,506.

Dec. 16, 2013 Office Action issued in U.S. Appl. No. 13/476,700.

Sep. 30, 2013 Extended European Search Report issued in Application No. 12003989.6.

Sep. 12, 2013 Office Action issued in U.S. Appl. No. 13/476,700.

* cited by examiner

SULFONIUM SALT, POLYMER, CHEMICALLY AMPLIFIED RESIST COMPOSITION USING SAID POLYMER, AND RESIST PATTERNING PROCESS

BACKGROUND OF THE INVENTION

1. Field of the Invention

The present invention relates to; a chemically amplified resist composition that is sensitive to a high energy beam such as an ultraviolet beam, a deep-ultraviolet beam, an electron beam, an EUV (extreme ultraviolet beam), an X-ray, a γ-beam, and a synchrotron radiation beam and is usable for processing of a semiconductor, a photomask blanks, and so on; especially a sulfonium salt usable to prepare a chemically amplified resist composition, especially a chemically amplified positive resist composition, that is used in a photo-exposure step by a beam irradiation of a high energy beam including an electron beam and a deep-ultraviolet beam; a polymer; a chemically amplified resist composition, especially a chemically amplified positive resist composition, using the said polymer; and a resist patterning process using the same.

2. Description of the Related Art

In recent years, as an integrated circuit progresses toward further higher integration, a further finer pattern profile is required; and thus, a chemically amplified resist using an acid as a catalyst is mainly used in the patterning process of the size of 0.2 µm or less. In this method, a high energy beam, such as an ultraviolet beam, a deep-ultraviolet beam, and an electron beam, is used as a light source for it; and especially an electron beam lithography used as an ultrafine processing technology has become indispensable also as a processing method of a photomask blank used for producing a photomask for a semiconductor manufacturing.

Generally, an electron beam drawing is carried out by an electron beam with a method wherein, in the case of a positive type, an electron beam with a fine area irradiates progressively, without using a mask, on an area other than those areas where a resist film is intended to be remained. In this method, an entire area of a processing surface that is finely divided is scanned, whereby taking more time as compared with a one-time exposure using a photomask; and thus, a high sensitivity resist film is required so that the throughput thereof may not be impaired. In addition, because the drawing takes a long time, difference between the parts drawn in earlier time and in later time tends to occur easily; and thus, temporary stability of an exposed part under vacuum is an important functional requirement item. In processing of a photomask blanks, which is an especially important application thereof, there is a case that a surface material affects a pattern profile of a chemically amplified resist easily, such as, for example, a film of a chromium compound including a chromium oxide formed on a photomask substrate; and thus, to keep rectangularity of a pattern profile of a resist film regardless of kinds of the substrate is also one important function for a high resolution and to keep a profile after etching.

Meanwhile, many improvements have been made in resist sensitivity and control of a pattern profile as mentioned above by selecting or combining materials used in a resist composition, process conditions, and so on. One item of such improvements relates to the issue of acid diffusion that has substantial influence on resolution of a chemically amplified resist. In a photomask processing, a resist pattern profile obtained as mentioned above needs to be unchanged regardless of the time passage after exposure to post-exposure baking; and here, a major cause for this change with the time passage is diffusion of an acid generated by the photo-exposure. Many studies have been made on the issue of the acid diffusion because this influences sensitivity and resolution not only in a photo mask-processing but also in a general resist composition.

Especially a method wherein the diffusion is suppressed by bonding a sulfonic acid generated by photo-exposure to a resin used in a resist composition, as disclosed in Japanese Patent Laid-Open (kokai) No. H09-325497, receives an attention as a suppression method that is based on a mechanism different from the suppression method using a basic compound. As the need for a further finer pattern increases, many attempts to improve this method have been made; the method described in Japanese Patent Laid-Open (kokai) 2008-133448 is an example of an attempt to improve an acid strength.

Meanwhile, a polymer containing many aromatic skeletons having an acidic side chain, for example, polyhydroxy styrene, has been used effectively as a resist material for a KrF excimer laser; but it has not been used as a resist material for an ArF excimer laser because it has a large absorption in wavelength of near 200 nm of the light. Nevertheless, in view of its high etching resistance, it is an important resist material for an electron beam and an EUV (extreme ultraviolet), which are useful technologies to form a smaller pattern than a processing limit by an ArF excimer laser.

As a base polymer for a positive type electron beam resist composition and EUV resist composition, a material whose acid-labile protective group that protects an acidic functional group of a phenolic side chain contained in the base polymer is deprotected by an acid catalyst generated from a photo acid generator by exposure thereof to a high energy beam thereby being made soluble in an alkaline developer is mainly used. As the acid-labile protective group mentioned above, a tertiary alkyl group, a t-butoxycarbonyl group, an acetal group, and the like have been mainly used. Here, when a protective group having a comparatively small activation energy necessary for deprotection, such as for example, an acetal group, is used, even though there is a merit of obtaining a highly sensitive resist film, the deprotection reaction takes place even in an unexposed part of the resist film if suppression of the generated acid-diffusion is insufficient, thereby causing a problem of deterioration of line edge roughness (LER) and decrease in in-plane uniformity of the pattern line width (that is, CDU (Critical Dimension Uniformity)).

The method for suppressing acid diffusion by bonding a repeating unit generating an acid by photo-exposure to a base polymer as shown in the foregoing Japanese Patent Laid-Open (kokai) Nos. H09-325497 and 2008-133448 is effective to obtain a pattern having a small LER. However, depending on the structure of the repeating unit mentioned above, there has been a case to cause a problem of poor solubility of the base polymer having the repeating unit to generate an acid by photo-exposure in a solvent. There has also been a problem of forming a pattern with a large LER when a resin has a repeating unit to generate an acid of high pKa such as a fluorinated alkanesulfonic acid and a repeating unit having an acetal group. That is, this is because the acetal group, which has relatively low activation energy for deprotection, is deprotected due to too high acidity of a minute amount of the fluorinated alkanesulfonic acid diffused to an unexposed part, even if acid diffusion is suppressed. In addition, there have been problems of easily causing pattern peel-off and pattern fall because a polymer containing a large amount of fluorine impairs adhesion with a substrate.

SUMMARY OF THE INVENTION

The present invention was made in view of the situation mentioned above, and has an object to provide; a sulfonium salt capable of introducing an acid-generating unit generating an acid having an appropriate acid strength and not impairing adhesion with a substrate into a base polymer; a polymer using the said sulfonium salt; a chemically amplified resist composition using the said polymer as a base polymer; and a patterning process using the said chemically amplified resist composition.

To solve the problems mentioned above, according to the present invention, provided is a sulfonium salt shown by the following general formula (1), (1)

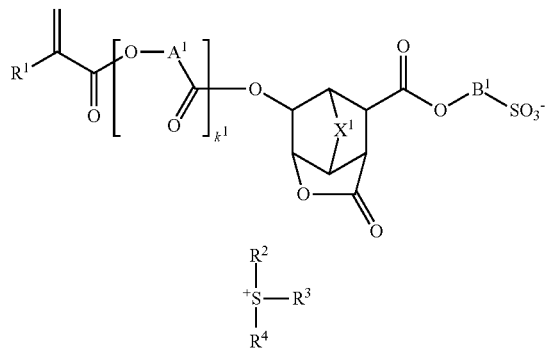

wherein, $R^1$ represents any of a hydrogen atom, a fluorine atom, a methyl group, and a trifluoromethyl group. Each $R^2$, $R^3$, and $R^4$ independently represents any of a substituted or unsubstituted linear, branched, or cyclic alkyl group, alkenyl group, and oxoalkyl group having 1 to 10 carbon atoms; any of a substituted or unsubstituted aryl, aralkyl, and aryl oxoalkyl group having 6 to 18 carbon atoms; or any two or more of $R^2$, $R^3$, and $R^4$ may be bonded with each other to form a ring together with a sulfur atom in the formula. $X^1$ represents O or $CH_2$. $A^1$ represents a linear, a branched, or a cyclic divalent hydrocarbon group having 1 to 10 carbon atoms. $B^1$ represents an alkylene group having 1 to 10 carbon atoms or an arylene group having 6 to 18 carbon atoms wherein these groups may contain an ether oxygen atom. $k^1$ represents an integer of 0 or 1.

The sulfonium salt shown by the general formula (1) is a sulfonium salt that can generate an acid having an appropriate acid strength and can introduce an acid-generating unit not impairing adhesion with a substrate into a base polymer of a chemically amplified resist composition. Therefore, according to the chemically amplified resist composition containing a polymer introduced with the repeating unit having the sulfonium salt as a base polymer, a resist film having excellent adhesion with a substrate can be obtained; and in addition, a pattern having a small line edge roughness can be formed by photo-exposure.

In addition, according to the present invention, provided is a polymer having a repeating unit shown by the following general formula (2) and a repeating unit shown by the following general formula (3), (2)

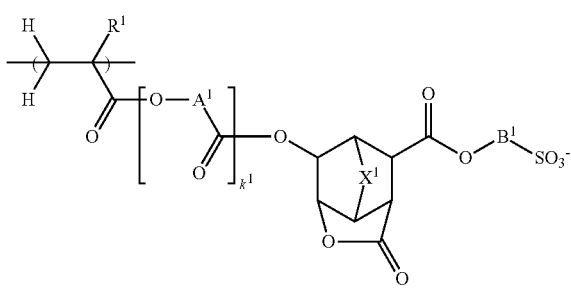

wherein, $R^1$ represents any of a hydrogen atom, a fluorine atom, a methyl group, and a trifluoromethyl group. Each $R^2$, $R^3$, and $R^4$ independently represents any of a substituted or unsubstituted linear, branched, or cyclic alkyl group, alkenyl group, and oxoalkyl group having 1 to 10 carbon atoms; any of a substituted or unsubstituted aryl, aralkyl, and aryl oxoalkyl group having 6 to 18 carbon atoms; or any two or more of $R^2$, $R^3$, and $R^4$ may be bonded with each other to form a ring together with a sulfur atom in the formula. $X^1$ represents O or $CH_2$. $A^1$ represents a linear, a branched, or a cyclic divalent hydrocarbon group having 1 to 10 carbon atoms. $B^1$ represents an alkylene group having 1 to 10 carbon atoms or an arylene group having 6 to 18 carbon atoms wherein these groups may contain an ether oxygen atom. $k^1$ represents an integer of 0 or 1.

(3)

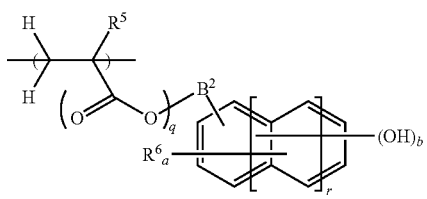

wherein, "q" represents 0 or 1. "r" represents an integer of 0 to 2. $R^5$ represents any of a hydrogen atom, a fluorine atom, a methyl group, and a trifluoromethyl group; and each $R^6$ independently represents a hydrogen atom or an alkyl group having 1 to 6 carbon atoms. $B^2$ represents a single bond or an alkylene group having 1 to 10 carbon atoms and optionally containing an ether bond. "a" represents an integer satisfying $a \le 5 + 2r - b$. "b" represents an integer of 1 to 3.

Consequently, according to the chemically amplified resist composition containing the polymer having the repeating unit shown by the general formula (2) and the repeating unit shown by the general formula (3) that provides the polymer with an adhesive property due to polarity contained therein, a resist film having excellent adhesion with a substrate can be obtained, and in addition, a pattern having a small line edge roughness can be formed by photo-exposure. Further in addition, the polymer like this can have a desirable solubility to an organic solvent so that this may be made into a coating composition easily.

In this case, it is preferable that the polymer contain further a repeating unit shown by the following general formula (4) as the unit to make the polymer alkaline-soluble by the action of an acid that is protected by an acid-labile group, (4)

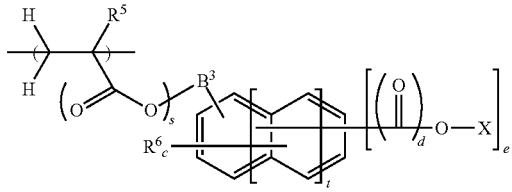

wherein, "s" represents 0 or 1. "t" represents an integer of 0 to 2. $R^5$ and $R^6$ represent the same meanings as before. $B^3$ represents a single bond or an alkylene group having 1 to 10 carbon atoms and optionally containing an ether bond. "c"

represents an integer satisfying c≤5+2t–e. "d" represents 0 or 1 and "e" represents an integer of 1 to 3. X represents an acid-labile group when "e" is 1; and a hydrogen atom or an acid-labile group when "e" is 2 or more, while at least one of X is an acid-labile group.

As mentioned above, when the polymer contains further the repeating unit shown by the general formula (4) as the unit to make the polymer alkaline-soluble by the action of an acid that is protected by an acid-labile group is used, a resist composition especially useful as a positive type can be obtained.

In this case, it is preferable that the polymer contain further a repeating unit shown by the following general formulae (5) and/or (6),

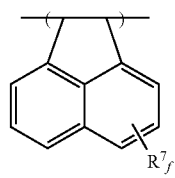

(5)

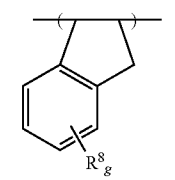

(6)

wherein, "f" represents an integer of 0 to 6, and each $R^7$ independently represents any of a hydrogen atom, an alkyl group or a primary or a secondary alkoxy group having 1 to 6 carbon atoms and optionally substituted with a halogen atom, and an alkylcarbonyloxy group having 1 to 7 carbon atoms and optionally substituted with a halogen atom. "g" represents an integer of 0 to 4; and each $R^8$ independently represents any of a hydrogen atom, an alkyl group or a primary or a secondary alkoxy group having 1 to 6 carbon atoms and optionally substituted with a halogen atom, and an alkylcarbonyloxy group having 1 to 7 carbon atoms and optionally substituted with a halogen atom.

As mentioned above, when the polymer contains further at least one or more of the repeating units shown by the general formulae (5) and (6), an effect of enhancing resistance to an electron beam during the time of etching and pattern inspection, in addition to enhancing the etching resistance due to the aromatic ring, can be obtained due to the ring structures added to the polymer's main chain.

In addition, the present invention provides a chemically amplified resist composition wherein the polymer is contained therein as a base polymer.

The polymer of the present invention has a good solubility to an organic solvent; and thus, the polymer is useful for a chemically amplified resist composition, especially for a chemically amplified resist composition of a positive type. When the composition containing the polymer of the present invention as a base polymer is used, a resist film having excellent adhesion with a substrate can be obtained; and in addition, a pattern having a small line edge roughness can be formed by photo-exposure.

In addition, the present invention provides a resist patterning process wherein the process comprises a step of forming a resist film on a substrate to be processed by using the chemically amplified resist composition, a step of pattern-exposure to a high energy beam, and a step of obtaining a resist pattern by developing with an alkaline developer.

When the resist patterning process of the present invention is used, good adhesion with a substrate as well as a pattern having small line edge roughness can be obtained.

In this case, it is preferable that an EUV or an electron beam be used as the high energy beam. The chemically amplified resist composition containing the polymer of the present invention as a base polymer is especially suitable for an electron beam lithography and an EUV lithography, which require high sensitivity in the resist film.

In addition, the substrate to be processed comprises a chromium-containing material in its outermost surface. Further in addition, a photomask blank may be used as the substrate to be processed.

As mentioned above, when the chemically amplified resist composition of the present invention is used, even if a substrate to be processed having a surface material easily affecting a pattern profile of a chemically amplified resist, such as a chromium-containing material in its outermost surface (for example photomask blank), is used, a resist film having excellent adhesion with the substrate can be obtained; and in addition, a pattern having a small line edge roughness can be formed by photo-exposure.

The polymer introduced with the sulfonium salt of the present invention as a repeating unit can be made into a coating composition easily; and when the polymer is used as a base polymer of a chemically amplified resist composition, excellent adhesion with a substrate, extremely high resolution, and a pattern with a small LER can be obtained in a microprocessing technology, especially in electron beam lithography and EUV lithography.

DETAILED DESCRIPTION OF THE PREFERRED EMBODIMENTS

Hereinafter, the present invention will be explained more specifically.

Inventors of the present invention carried out extensive studies to accomplish the object mentioned above; and as a result, they found that, when a chemically amplified resist polymer containing, for example, as a main constituting element, a repeating unit having an aromatic ring as shown by the general formulae (3) to (5) was introduced with a polymerizable anion-containing sulfonium salt shown by the general formula (1) as a repeating unit (namely, repeating unit (2)), desirable solubility of the polymer into an organic solvent was obtained and in addition acid diffusion in a resist film was suppressed during patterning, thereby obtaining a pattern with a small LER and a stable pattern even on a substrate to be processed having a material easily causing pattern peel-off and pattern fall during the time of patterning. With these findings, the present invention could be accomplished.

That is, the present invention provides a sulfonium salt described below, a polymer having the said sulfonium salt as a repeating unit, a chemically amplified resist composition containing the said polymer as a base polymer, and a patterning process.

Hereinafter, the present invention will be explained in detail. Meanwhile, in the following explanation, an asymmetric carbon may be present depending on the structure shown by a chemical formula, namely enantiomers and diastereomers may be present; but these isomers are expressed by a single formula as their representative. These isomers may be used singly or as a mixture of them.

The present invention provides a polymerizable anion-containing sulfonium salt shown by the following general formula (1),

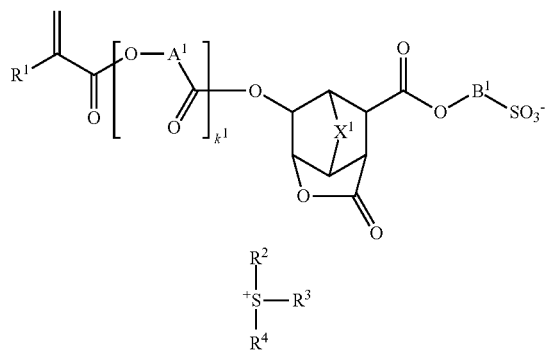

(1)

wherein, $R^1$ represents any of a hydrogen atom, a fluorine atom, a methyl group, and a trifluoromethyl group. Each $R^2$, $R^3$, and $R^4$ independently represents any of a substituted or unsubstituted linear, branched, or cyclic alkyl group, alkenyl group, and oxoalkyl group having 1 to 10 carbon atoms; any of a substituted or unsubstituted aryl, aralkyl, and aryl oxoalkyl group having 6 to 18 carbon atoms; or any two or more of $R^2$, $R^3$, and $R^4$ may be bonded with each other to form a ring together with a sulfur atom in the formula. $X^1$ represents (O) or $CH_2$. $A^1$ represents a linear, a branched, or a cyclic divalent hydrocarbon group having 1 to 10 carbon atoms. $B^1$ represents an alkylene group having 1 to 10 carbon atoms or an arylene group having 6 to 18 carbon atoms wherein these groups may contain an ether oxygen atom. $k^1$ represents an integer of 0 or 1.

Specific example of the alkylene group having 1 to 10 carbon atoms or the arylene group having 6 to 18 carbon atoms, wherein these groups may contain an ether oxygen atom, shown by $B^1$ in the general formula (1), includes the followings, though not limited to them,

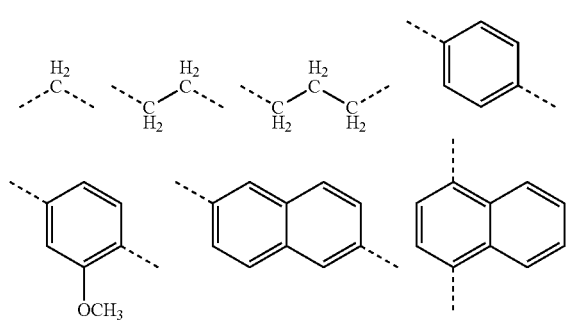

wherein, broken lines show bonding hands.

In the general formula (1), $A^1$ represents a linear, a branched, or a cyclic divalent hydrocarbon group having 1 to 10 carbon atoms; and specific example thereof includes the followings.

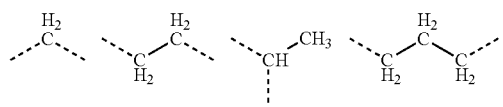

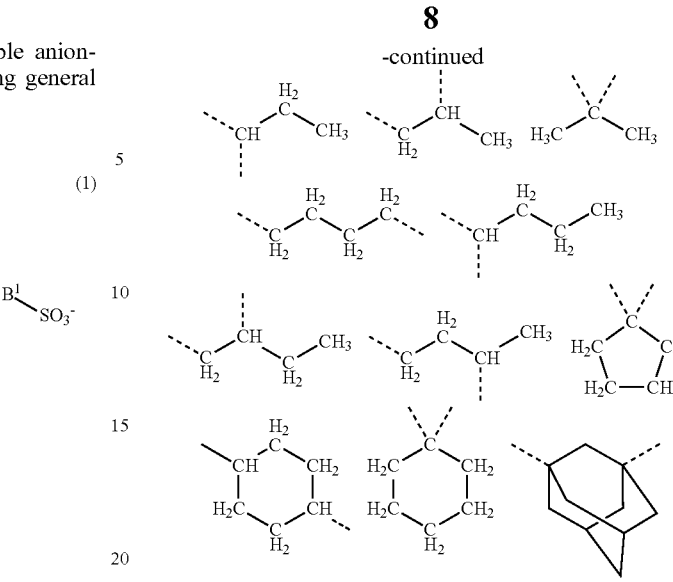

In the general formula (1), each $R^2$, $R^3$, and $R^4$ independently represents any of a substituted or unsubstituted linear, branched, or cyclic alkyl group, alkenyl group, and oxoalkyl group having 1 to 10 carbon atoms; any of a substituted or unsubstituted aryl, aralkyl, and aryl oxoalkyl group having 6 to 18 carbon atoms; or any two or more of $R^2$, $R^3$, and $R^4$ may be bonded with each other to form a ring together with a sulfur atom in the formula.

Specific example of the substituted or unsubstituted alkyl group includes a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methylcyclohexyl group, a cyclohexylmethyl group, a norbornyl group, and an adamantly group.

Example of the substituted or unsubstituted alkenyl group includes a vinyl group, an allyl group, a propenyl group, a butenyl group, a hexenyl group, and a cyclohexenyl group.

Example of the substituted or unsubstituted oxoalkyl group includes a 2-oxocyclopentyl group, a 2-oxocyclohexyl group, a 2-oxopropyl group, a 2-oxoethyl group, a 2-cyclopentyl-2-oxoethyl group, a 2-cyclohexyl-2-oxoethyl group, and a 2-(4-methylcyclohexyl)-2-oxoethyl group.

Example of the substituted or unsubstituted aryl group includes a phenyl group, a naphthyl group, and a thienyl group; an alkoxyphenyl group such as a 4-hydroxy phenyl group, a 4-methoxy phenyl group, a 3-methoxy phenyl group, a 2-methoxy phenyl group, a 4-ethoxy phenyl group, a 4-tert-butoxy phenyl group, and a 3-tert-butoxy phenyl group; an alkyl phenyl group such as a 2-methyl phenyl group, a 3-methyl phenyl group, a 4-methyl phenyl group, a 4-ethyl phenyl group, a 4-tert-butyl phenyl group, a 4-n-butyl phenyl group, and a 2,4-dimethyl phenyl group; an alkyl naphthyl group such as a methyl naphthyl group and an ethyl naphthyl group; an alkoxy naphthyl group such as a methoxy naphthyl group and an ethoxy naphthyl group; a dialkyl naphthyl group such as a dimethyl naphthyl group and a diethyl naphthyl group; and a dialkoxy naphthyl group such as a dimethoxy naphthyl group and a diethoxy naphthyl group.

Example of the substituted or unsubstituted aralkyl group includes a benzyl group, a 1-phenylethyl group, and a 2-phenylethyl group.

Example of the substituted or unsubstituted aryl oxoalkyl group includes a 2-aryl-2-oxoethyl group such as a 2-phenyl-2-oxoethyl group, a 2-(1-naphthyl)-2-oxoethyl group, and a 2-(2-naphthyl)-2-oxoethyl group.

As to the case that any two or more of $R^2$, $R^3$, and $R^4$ are bonded with each other to form a ring together with a sulfur atom in the formula, example thereof includes the groups shown by the following formulae.

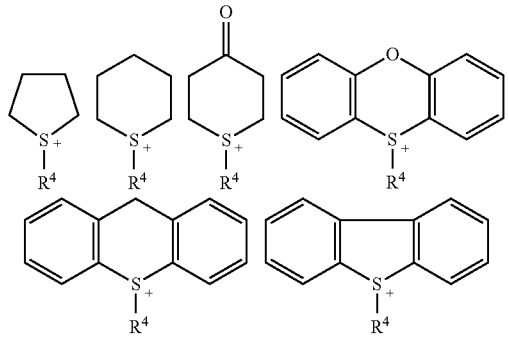

More specific example of the sulfonium cation in the general formula (1) includes a triphenyl sulfonium, a 4-hydroxyphenyl diphenyl sulfonium, a bis(4-hydroxyphenyl)phenyl sulfonium, a tris(4-hydroxyphenyl) sulfonium, a 4-tert-butoxyphenyl diphenyl sulfonium, a bis(4-tert-butoxyphenyl) phenyl sulfonium, a tris(4-tert-butoxyphenyl) sulfonium, a 3-tert-butoxyphenyl diphenyl sulfonium, a bis(3-tert-butoxyphenyl)phenyl sulfonium, a tris(3-tert-butoxyphenyl) sulfonium, a 3,4-di-tert-butoxyphenyl diphenyl sulfonium, a bis(3,4-di-tert-butoxyphenyl)phenyl sulfonium, a tris(3,4-di-tert-butoxyphenyl) sulfonium, a diphenyl (4-thiophenoxyphenyl) sulfonium, a 4-tert-butoxycarbonylmethyloxyphenyl diphenyl sulfonium, a tris(4-tert-butoxycarbonylmethyloxyphenyl) sulfonium, a (4-tert-butoxyphenyl)bis(4-dimethylaminophenyl) sulfonium, a tris(4-dimethylaminophenyl) sulfonium, a 2-naphthyl diphenyl sulfonium, a (4-hydroxy-3,5-dimethylphenyl)diphenyl sulfonium, a (4-n-hexyloxy-3,5-dimethylphenyl)diphenyl sulfonium, a dimethyl (2-naphthyl) sulfonium, a 4-hydroxyphenyl dimethyl sulfonium, a 4-methoxyphenyl dimethyl sulfonium, a trimethyl sulfonium, a 2-oxocyclohexyl cyclohexyl methyl sulfonium, a trinaphthyl sulfonium, a tribenzyl sulfonium, a diphenyl methyl sulfonium, a dimethyl phenyl sulfonium, a 2-oxo-2-phenylethyl thiacyclopentanium, a diphenyl 2-thienyl sulfonium, a 4-n-butoxynaphthyl-1-thiacyclopentanium, a 2-n-butoxynaphthyl-1-thiacyclopentanium, a 4-methoxynaphthyl-1-thiacyclopentanium, and a 2-methoxynaphthyl-1-thiacyclopentanium.

More preferable example thereof includes a triphenyl sulfonium, a 4-tert-butylphenyl diphenyl sulfonium, a 4-tert-butoxyphenyl diphenyl sulfonium, a tris(4-tert-butylphenyl) sulfonium, a tris(4-tert-butoxyphenyl) sulfonium, and dimethyl phenyl sulfonium.

Specific preferable example of the sulfonium salt shown by the general formula (1) includes the followings,

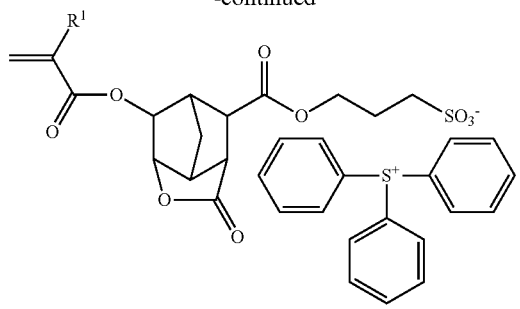

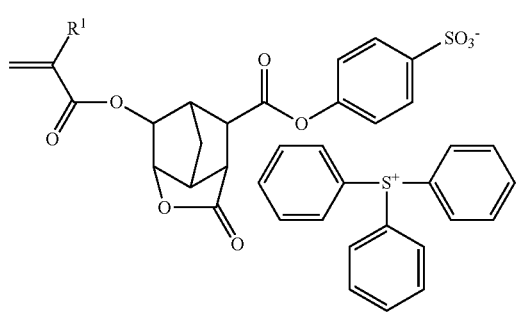

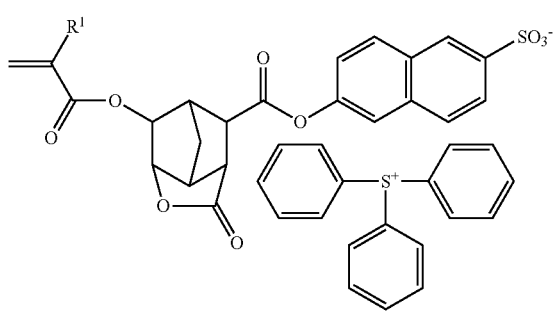

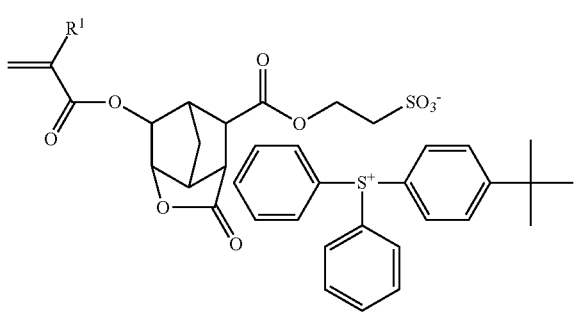

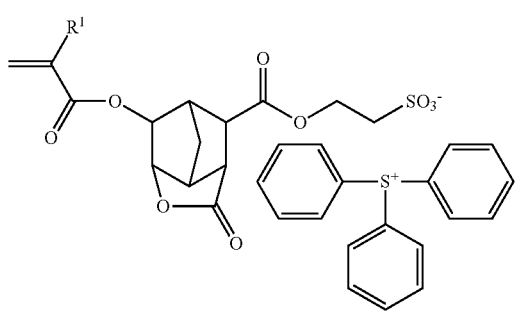

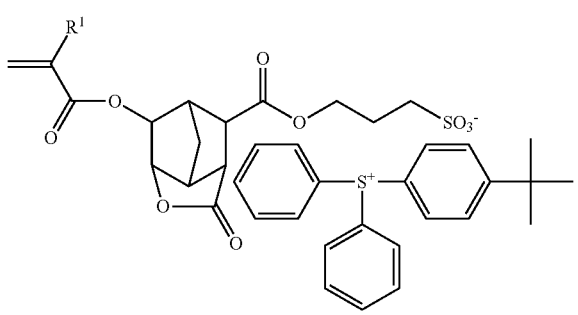

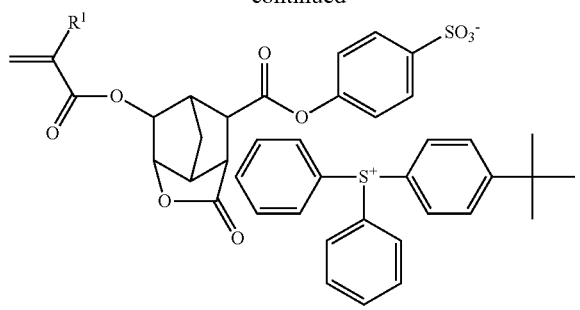
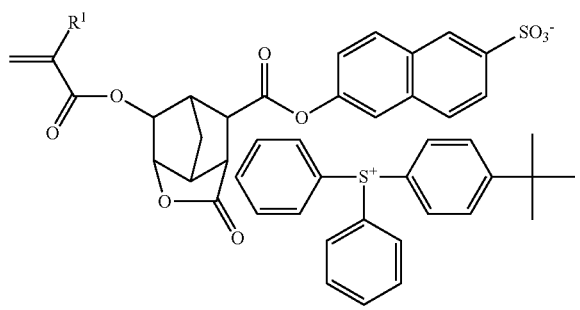
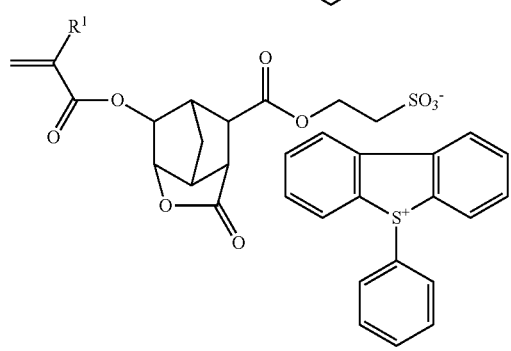
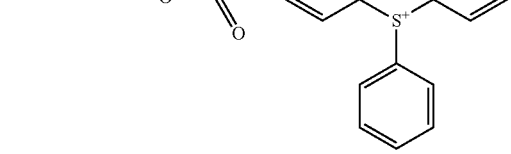
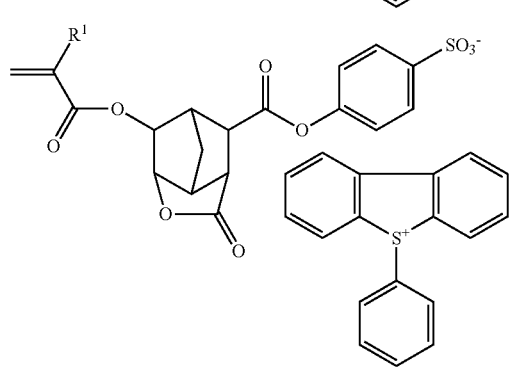
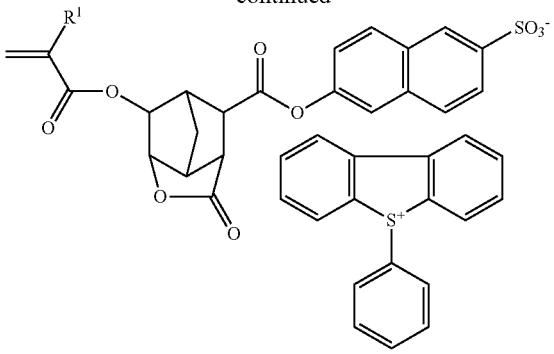
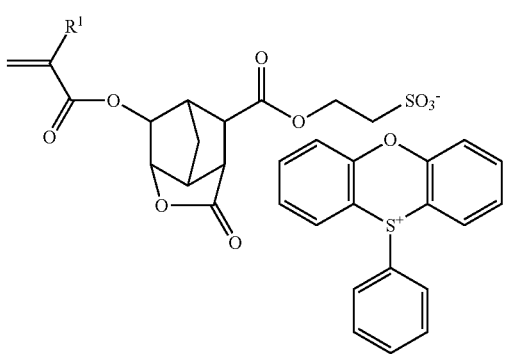
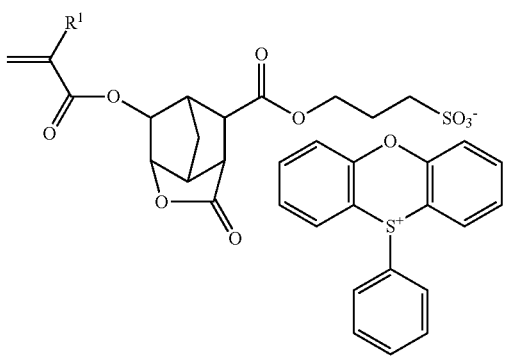
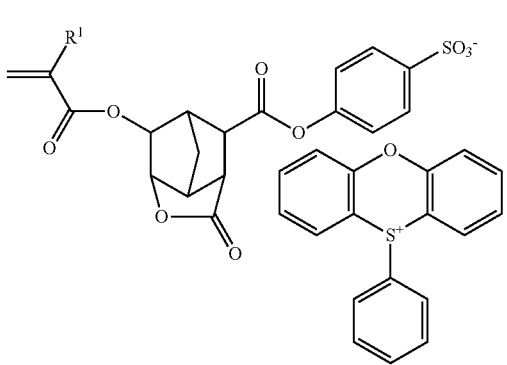
wherein, $R^1$ represents the same meanings as described before.

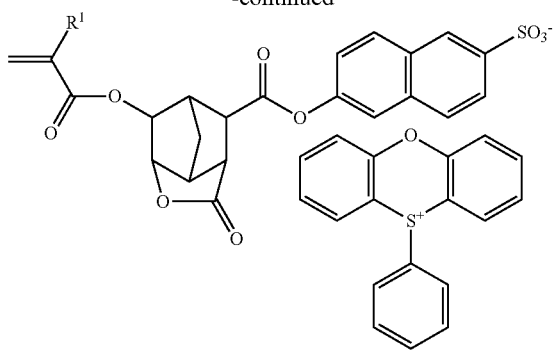
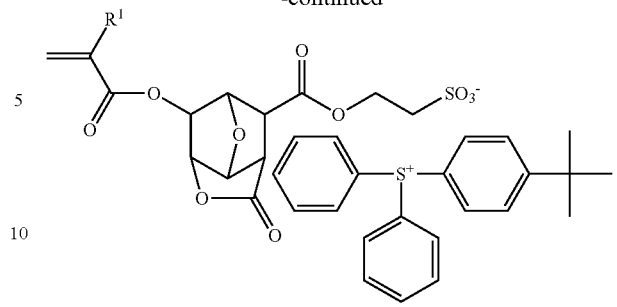
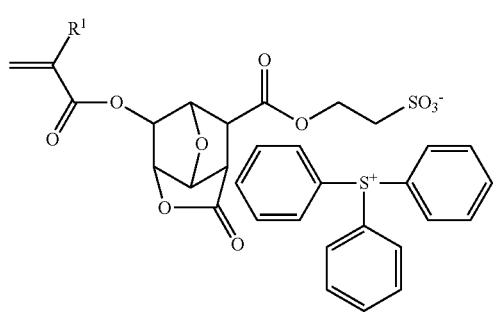
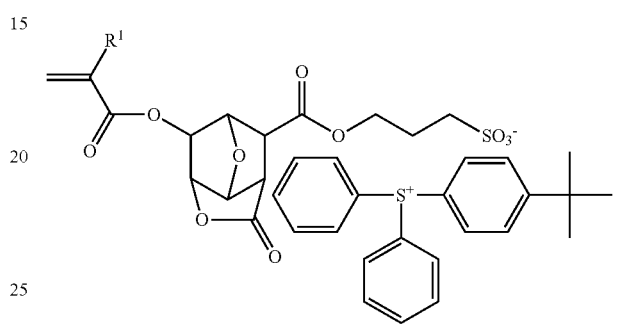
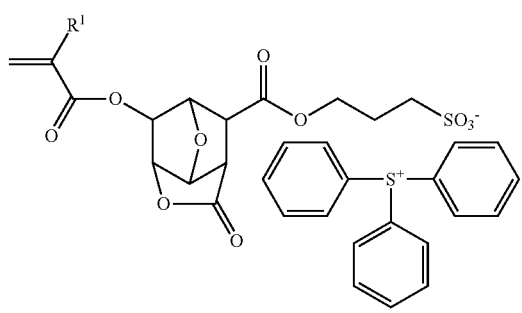
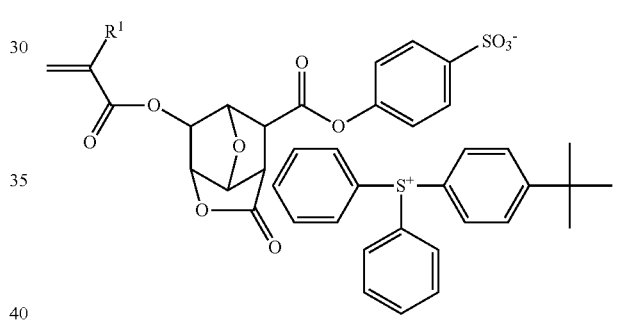
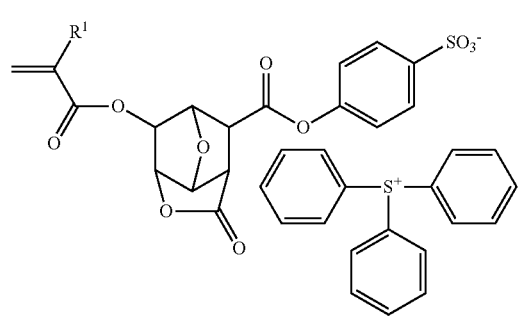
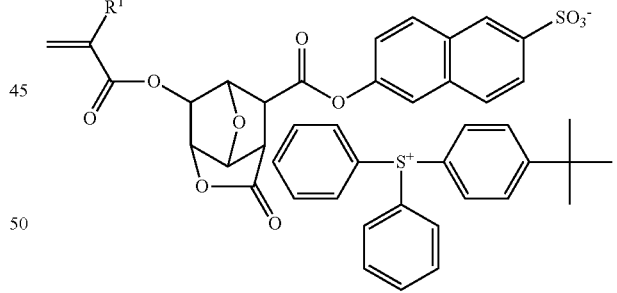
wherein, $R^1$ represents the same meanings as described before.
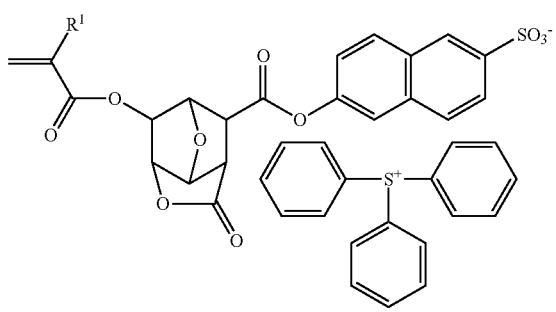
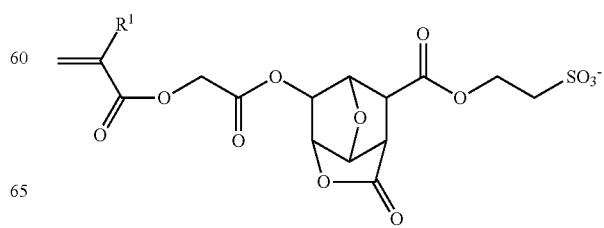

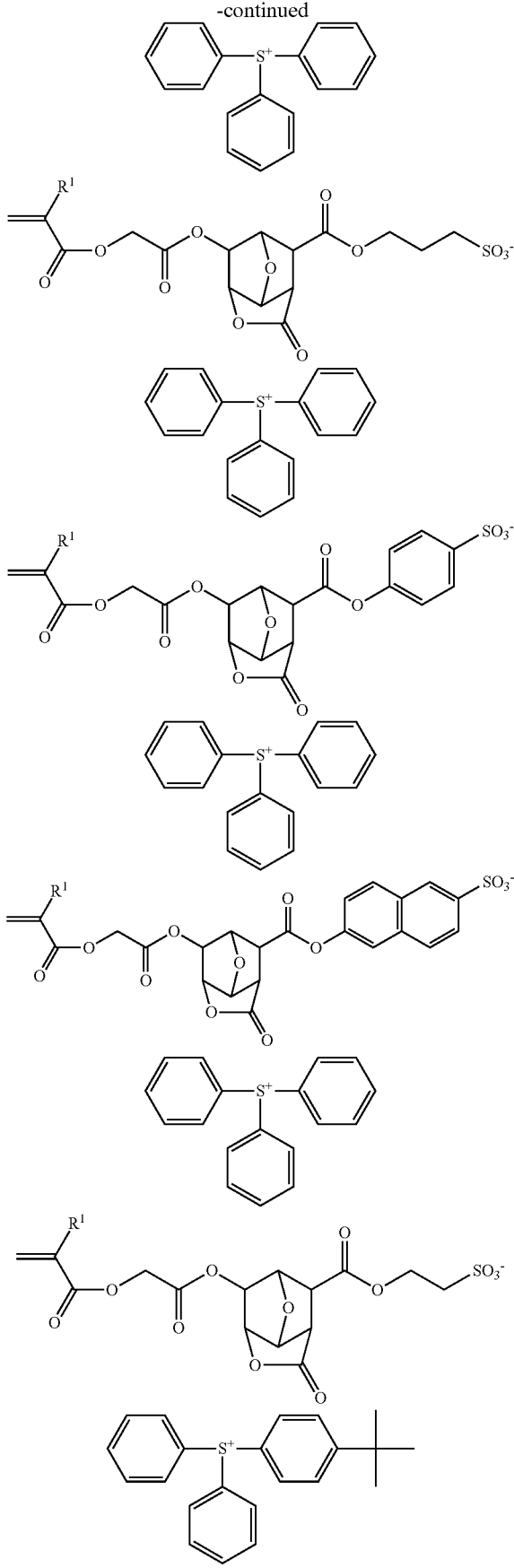
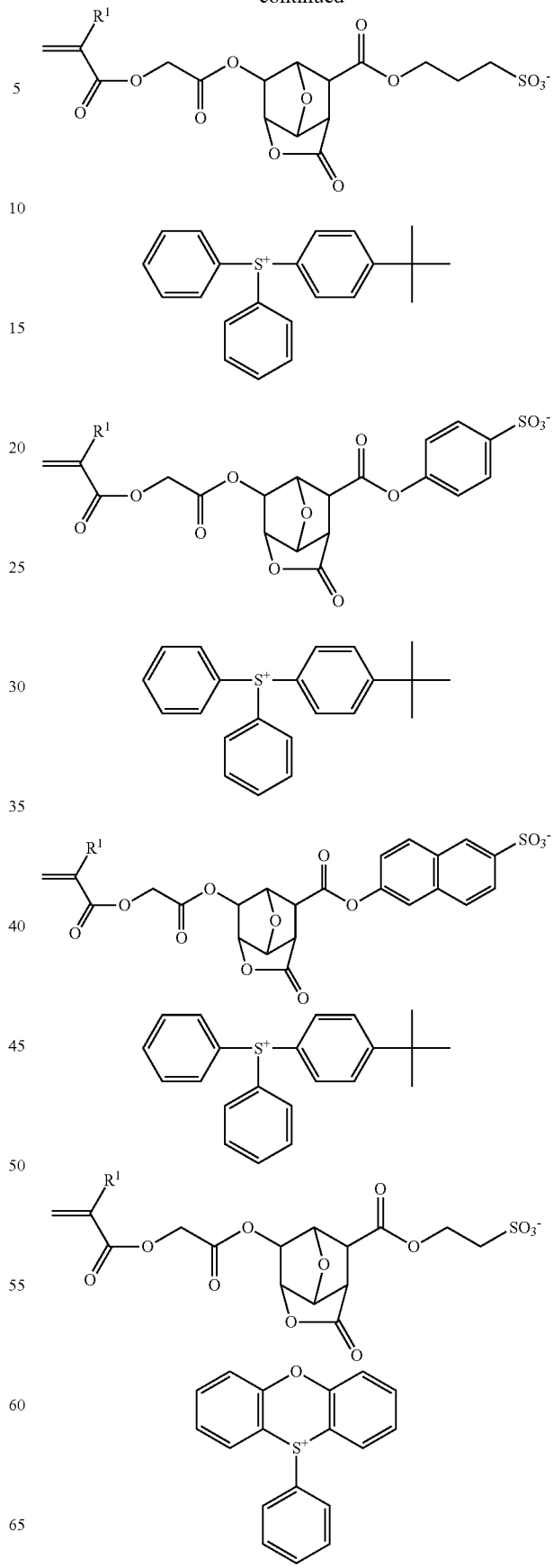

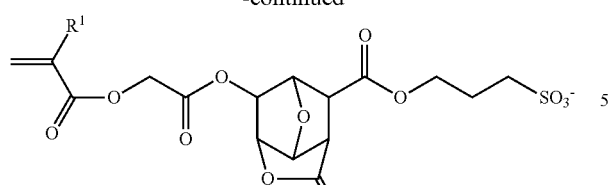
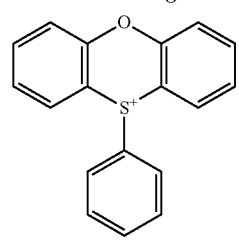
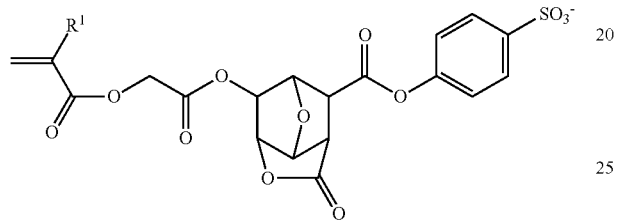
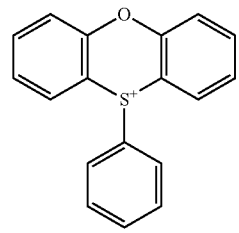
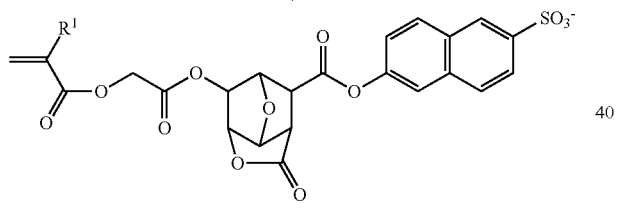
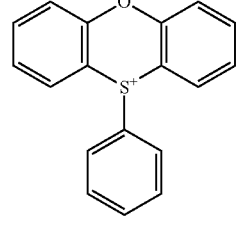
wherein, $R^1$ represents the same meanings as described before.
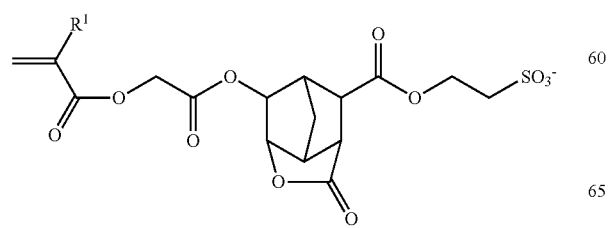
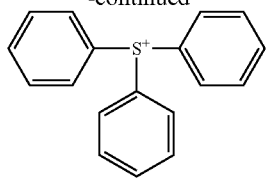
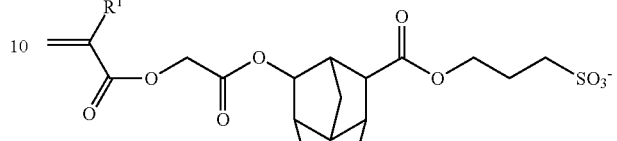
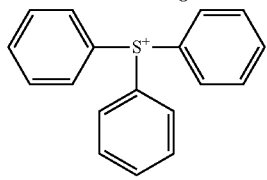
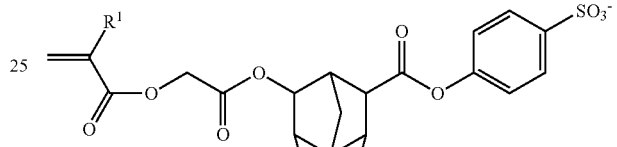
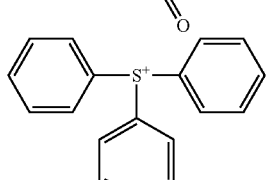
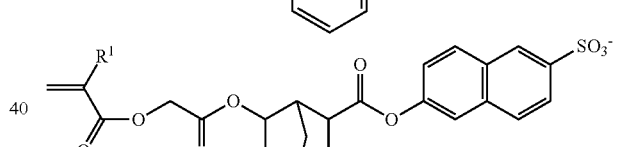
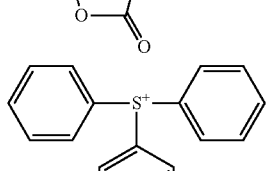
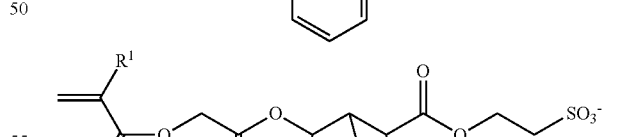
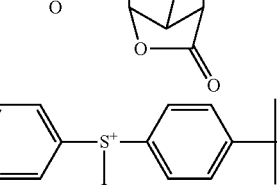

wherein, R¹ represents the same meanings as described before.

Illustrative example of the method to obtain the sulfonium salt (monomer) shown by the general formula (1) is as following, though not limited to it. Hereinafter, the broken lines shown in the formulae indicate bonding hands,

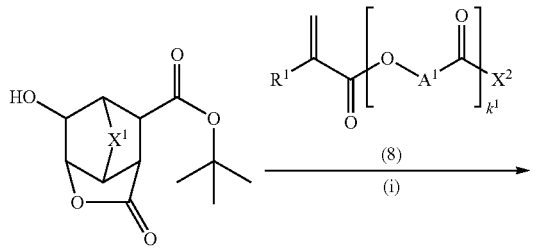

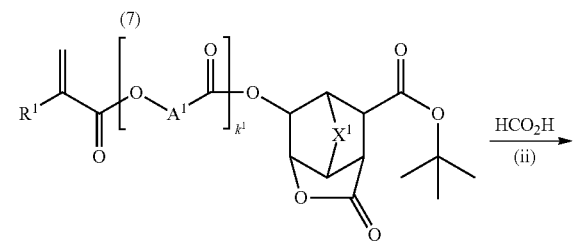

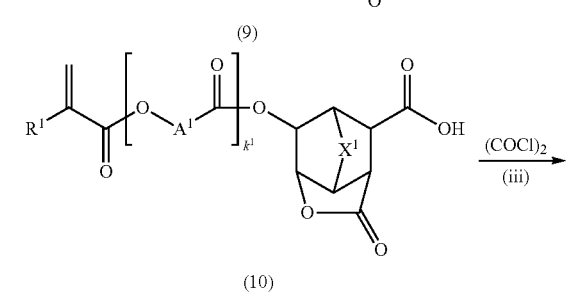

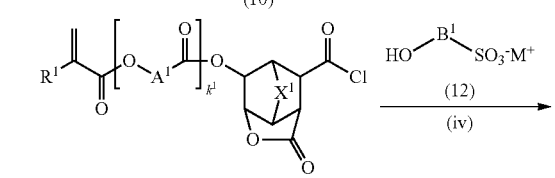

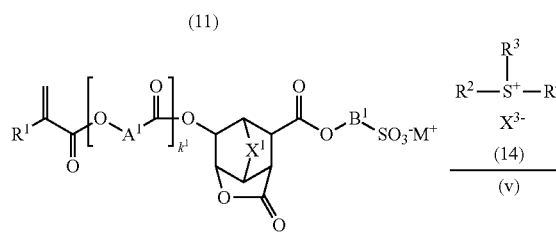

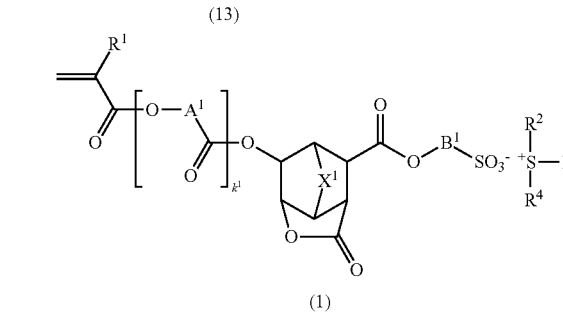

wherein, $R^1$ to $R^4$, $X^1$, $A^1$, $B^1$, and $k^1$ represent the same meanings as before. $X^2$ represents a halogen atom, a hydroxyl group, an alkoxy group, or a substituent shown by the following general formula (15),

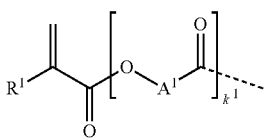

($R^1$, $A^1$, and $k^1$ represent the same meanings as before.) $M^+$ represents any of a lithium ion, a sodium ion, a potassium ion, and a substituted or unsubstituted ammonium ion. $X^{3-}$ represents a halide ion or a methylsulfate ion.

Meanwhile, in the case that $k^1$ in the general formula (1) is 1, the compound (9) in the foregoing chemical reaction scheme can be obtained by the different method shown below,

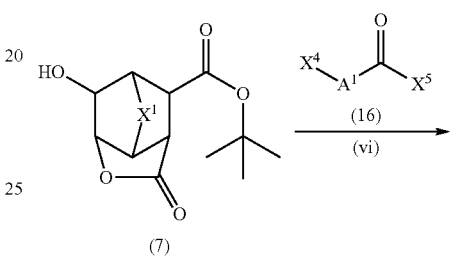

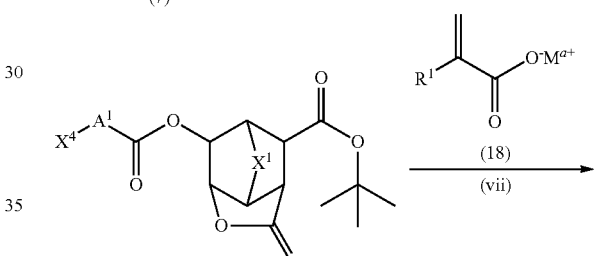

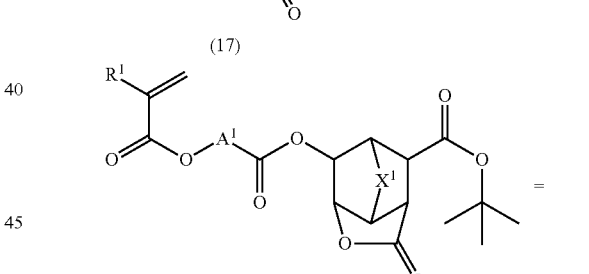

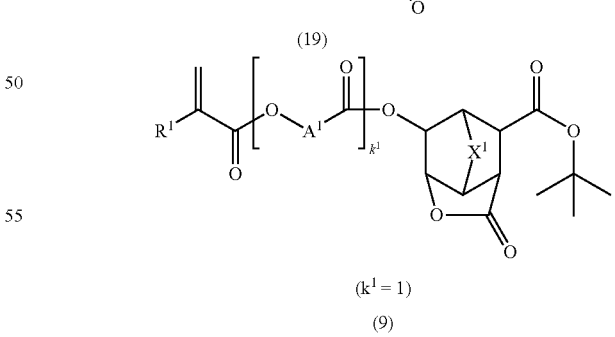

wherein, $X^1$, $R^1$, and $A^1$ represent the same meanings as before. $X^4$ represents a halogen atom. $X^5$ represents a halogen atom, a hydroxyl group, or an alkoxy group. $M^{a+}$ represents a lithium ion, a sodium ion, a potassium ion, a magnesium ion, a calcium ion, or a substituted or unsubstituted ammonium ion.

In the step (i), a hydroxyl lactone (7) is reacted with an esterification agent (8) to give the ester (9). Here, details of a synthesis method of the hydroxyl lactone (7) are described in Japanese Patent Laid-Open (kokai) No. 2000-159758 and Japanese Patent No. 4539865.

This reaction proceeds easily by a conventional method; and as to the esterification agent (8), an acid chloride (the case of $X^2$ in the formula (8) being a chlorine atom), an acid anhydride (the case of $X^2$ in the formula (8) being a substituent shown by the general formula (15)) or a carboxylic acid (the case of $X^2$ in the formula (8) being a hydroxyl group) is preferable.

In the case that an acid chloride or an acid anhydride is used as the esterification agent, the reaction may be suitably carried out as following; the hydroxyl lactone compound (7), a corresponding acid chloride or acid anhydride such as acryloyl chloride, methacryloyl chloride, acrylic anhydride, and methacrylic anhydride, and a base such as triethylamine, pyridine, and 4-dimethylaminopyridine are added sequentially or simultaneously into a solvent such as methylene chloride, toluene, hexane, diethyl ether, tetrahydrofurane, and acetonitrile or without using a solvent, and then the resulting mixture is heated or cooled as appropriate.

In the case that a carboxylic acid is used, the reaction may be suitably carried out as following; the hydroxyl lactone (7) and a corresponding carboxylic acid such as acrylic acid and methacylic acid are heated in the presence of an acid catalyst in a solvent such as toluene and hexane with removing generated water outside the system or the like if necessary. Illustrative example of the acid catalyst includes an inorganic acid such as hydrochloric acid, sulfuric acid, nitric acid, and perchloric acid, and an organic acid such as p-toluenesulfonic acid and benzenesulfonic acid.

In the step (ii), the tert-butyl group of the tert-butyl ester (9) is deprotected by formic acid to obtain a carboxylic acid (10). The ester (9) is dissolved into formic acid as the solvent for it; and the carboxylic acid (10) can be obtained with stirring and with cooling or heating the reaction solution as appropriate.

In the step (iii), the carboxylic acid (10) is transformed to a corresponding acid chloride (11). The reaction may be suitably carried out by adding a chlorinating agent such as oxalyl dichloride sequentially or simultaneously with the carboxylic acid into such a solvent as methylene dichloride, toluene, hexane, diethyl ether, tetrahydrofurane, and acetonitrile; and then the resulting mixture is cooled or heated as appropriate.

In the step (iv), a nucleophilic substitution reaction of the acid chloride (11) with a sulfo alcohol (12) is carried out to obtain an onium salt (13). The reaction may be suitably carried out according to a usual method by adding, sequentially or simultaneously, the acid chloride (11), the sulfo alcohol (12), and a base into a solvent, and then the resulting mixture is cooled or heated as appropriate.

Illustrative example of the solvent usable in the reaction includes; water; an ether such as tetrahydrofurane, diethyl ether, diisopropyl ether, di-n-butyl ether, and 1,4-dioxane; a hydrocarbon such as n-hexane, n-heptane, benzene, toluene, and xylene; a nonprotonic polar solvent such as acetonitrile, dimethyl sulfoxide (DMSO), and N,N-dimethylformamide (DMF); and a chlorinated organic solvent such as methylene chloride, chloroform, and carbon tetrachloride. These solvents may be appropriately selected according to a reaction condition, and may be used singly or as a mixture of two or more of them.

Illustrative example of the base usable in the reaction shown by the step (iv) includes an amine such as ammonia, triethylamine, pyridine, lutidine, collidine, and N,N-dimethylaniline; a hydroxide such as sodium hydroxide, potassium hydroxide, and tetramethyl ammonium hydroxide; and a carbonate such as potassium carbonate and sodium hydrogen carbonate. These bases may be used singly or as a mixture of two or more of them.

In the step (v), an ion-exchange reaction of the onium salt (13) with a sulfonium salt (14) is carried out to obtain the polymerizable anion-containing sulfonium salt (1). The onium salt (13) may be used after it is isolated by a usual post-treatment of an aqueous system after the reaction of step (iv) or without a particular post-treatment after stopping of the reaction.

In the case that the onium salt (13) once isolated is used, the onium salt (13) is dissolved into such a solvent as water, an ethers such as tetrahydrofurane, diethyl ether, diisopropyl ether, di-n-butyl ether, and 1,4-dioxane, a hydrocarbons such as n-hexane, n-heptane, benzene, toluene, and xylene, a nonprotonic polar solvents such as acetonitrile, dimethyl sulfoxide (DMSO), and N,N-dimethylformamide (DMF), and a chlorinated organic solvents such as methylene chloride, chloroform, and carbon tetrachloride, and then mixed with the sulfonium salt (14); the resulting mixture is cooled or heated as appropriate to obtain a reaction mixture. The polymerizable anion-containing sulfonium salt (1) can be obtained from this reaction mixture by a usual post-treatment of an aqueous system (aqueous work-up); and purification thereof can be carried out by a conventional method such as distillation, recrystallization, and chromatography, as appropriate.

In the case that the onium salt (13) obtained without particular post-treatment after termination of the synthesis reaction of the onium salt (13) is used, the polymerizable anion-containing sulfonium salt (1) can be obtained by adding the sulfonium salt (14) into the mixture obtained after termination of the synthesis reaction of the onium salt (13), followed by cooling or heating the resulting mixture as appropriate. At this time, a solvent including water, an ethers such as tetrahydrofurane, diethyl ether, diisopropyl ether, di-n-butyl ether, and 1,4-dioxane, a hydrocarbons such as n-hexane, n-heptane, benzene, toluene, and xylene, a nonprotonic polar solvents such as acetonitrile, dimethyl sulfoxide (DMSO), and N,N-dimethylformamide (DMF), and a chlorinated organic solvents such as methylene chloride, chloroform, and carbon tetrachloride may be added thereinto. The polymerizable anion-containing sulfonium salt (1) can be obtained from the reaction mixture by a usual aqueous work-up; and purification thereof can be carried out by a usual method such as distillation, recrystallization, and chromatography, as appropriate.

The steps (vi) and (vii) show an alternative method to obtain the ester (19) in the reaction scheme shown above in the case that $k^1$ represents 1 in the general formula (1).

In the step (vi), the hydroxyl lactone (7) is reacted with an esterification agent (16) to obtain a halo ester (17). The reaction proceeds easily by a heretofore known method; but an acid chloride (the case of $X^5$ being a chlorine atom in the formula (16)) or a carboxylic acid (the case of $X^5$ being a hydroxyl group in the formula (16)) is particularly preferable as the esterification agent (16).

In the case that an acid chloride is used, the reaction may be suitably carried out as following; the hydroxyl lactone (7), a corresponding acid chloride such as 2-chloroacety chloride and 3-chloropropionyl chloride, and a base such as triethylamine, pyridine, and 4-dimethylaminopyridine are added sequentially or simultaneously into a solvent such as methylene chloride, acetonitrile, toluene, and hexane or without using a solvent; and then, the resulting mixture is heated or cooled as appropriate.

In the case that a carboxylic acid is used, the reaction may be suitably carried out by heating the hydroxyl lactone (7) and a corresponding carboxylic acid such as 2-chloroacetic acid and 3-chloropropionic acid in the presence of an acid catalyst in a solvent such as toluene and hexane with removing generated water outside the system or the like if necessary.

Illustrative example of the acid catalyst to be used includes an inorganic acid such as hydrochloric acid, sulfuric acid, nitric acid, and perchloric acid, and an organic acid such as p-toluenesulfonic acid and benzenesulfonic acid. It is preferable that in view of the reaction yield, the reaction be stopped at the time when it is completed with following course of the reaction by a gas chromatography (GC) or a silica gel thin-layer chromatography (TLC); but the reaction time is usually about 0.5 to about 24 hours. The halo ester (17) can be obtained from the reaction mixture by a usual aqueous work-up; and purification thereof can be carried out by a conventional method such as distillation, recrystallization, and chromatography, if necessary.

The step (vii) is a reaction of the halo ester (17) with a carboxylic acid salt compound (18) to give the ester (19).

The reaction of the step (vii) may be carried out by a usual method. As to the carboxylic acid salt compound (18), a carboxylic acid salt compound such as various commercially available carboxylic acid metal salts may be used in the form as they are, or a carboxylic acid salt compound prepared in the reaction system from a corresponding carboxylic acid such as methacrylic acid and acrylic acid and a base may be used. Amount of the carboxylic acid salt compound (18) to be used is preferably 0.5 to 10 moles, or in particular 1.0 to 3.0 moles, relative to one mole of the raw material halo ester (17). When the use amount is less than 0.5 mole, there is a case of substantial decrease in the reaction yield because a large amount of the raw material remains; when the use amount is more than 10 moles, there is a disadvantageous case in cost because of an increased cost of the raw material and a lowered pot-yield. Illustrative example of the base to prepare the carboxylic acid salt compound from the corresponding carboxylic acid and the base in the reaction system includes an amine such as ammonia, triethylamine, pyridine, lutidine, collidine, and N,N-dimethylaniline; a hydroxide such as sodium hydroxide, potassium hydroxide, and tetramethyl ammonium hydroxide; a carbonate such as potassium carbonate and sodium hydrogen carbonate; a metal such as sodium; a metal hydride such as sodium hydride; a metal alkoxide such as sodium methoxide and potassium t-butoxide; an organometallic compound such as butyl lithium and ethyl magnesium bromide; and a metal amide such as lithium diisopropylamide; and they may be used singly or as a mixture of two or more of them. Amount of the base to be used is preferably 0.2 to 10 moles, or in particular 0.5 to 2.0 moles, relative to one mole of the corresponding carboxylic acid. When the amount is less than 0.2 mole, there is an disadvantageous case in cost because a large amount of the carboxylic acid is wasted; and when the amount is more than 10 moles, there is a case of substantial decrease in the reaction yield because a side reaction may increase. It is preferable that, in view of the reaction yield, the reaction be stopped when it is completed with following course of the reaction by a gas chromatography (GC) or a silica gel thin-layer chromatography (TLC); but the reaction time is usually about 0.5 to about 24 hours. The ester (19) can be obtained from the reaction mixture by a usual aqueous work-up; and purification thereof can be carried out by a usual method such as distillation, recrystallization, and chromatography, as appropriate.

The sulfonium salt of the present invention shown by general formula (1) has a lactone structure as well as a sulfonium salt structure of a sulfonic acid not substituted with a fluorine atom. Because of these structures, if it is introduced into a base polymer as its repeating unit used for a chemically amplified resist composition, an acid having an appropriate acid strength can be generated by exposure to a high energy beam, and in addition, migration and diffusion of the generated acid can be controlled suitably; and further, a resist film provided with a high adhesion with a substrate may be expected. Meanwhile, this sulfonium salt (monomer) has a sufficient lipophilicity; and thus, its production and handling are easy.

Meanwhile, in a similar manner to the synthesis method of the polymerizable anion-containing sulfonium salt shown by the general formula (1), a salt of iodonium, ammonium, or the like containing the polymerizable anion can be synthesized; and these onium salts may be introduced into a polymer of the present invention or into other polymers that will be explained later so that they may also be used for the chemically amplified resist composition.

More specific example of the iodonium cation includes a diphenyl iodonium, a bis(4-methylphenyl) iodonium, a bis(4-(1,1-dimethylethyl)phenyl) iodonium, a bis(4-(1,1-dimethylpropyl)phenyl) iodonium, and a (4-(1,1-dimethylethoxy)phenyl)phenyl iodonium; and example of the ammonium salt includes a salt of a tertiary ammonium such as a trimethyl ammonium, a triethyl ammonium, a tributyl ammonium, and a N,N-dimethyl anilinium, and a salt of a quaternary ammonium such as a tetramethyl ammonium, a tetraethyl ammonium, and a tetrabutyl ammonium. Polymerizable anion-containing iodonium salt described above and a polymer containing this as a repeating unit are used as a photo acid generator or a thermal acid generator, and a polymerizable anion-containing ammonium salt and a polymer containing this as a repeating unit are used as a thermal acid generator.

According to the present invention, provided, as a polymer usable to prepare a resist composition, is a polymer containing a repeating unit shown by the following general formula (2) derived from the sulfonium salt (monomer) that generates the acid and a repeating unit shown by the following general formula (3) that provides the polymer with an adhesion property with a substrate by having a polarity within its molecular structure,

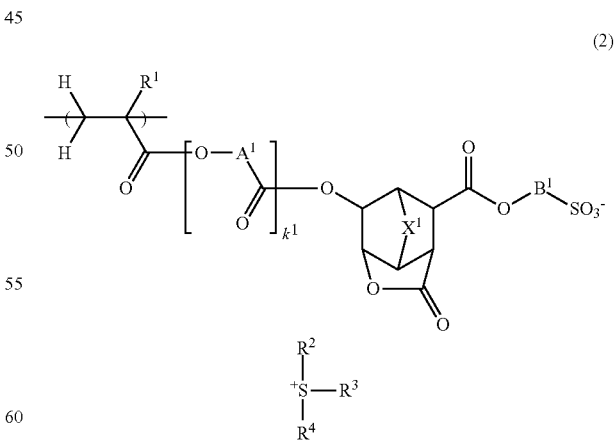

(2)

wherein, $R^1$ represents any of a hydrogen atom, a fluorine atom, a methyl group, and a trifluoromethyl group. Each $R^2$, $R^3$, and $R^4$ independently represents any of a substituted or unsubstituted linear, branched, or cyclic alkyl group, alkenyl group, and oxoalkyl group having 1 to 10 carbon atoms; any of a substituted or unsubstituted aryl, aralkyl, and aryl oxoalkyl group having 6 to 18 carbon atoms; or any two or more of $R^2$, $R^3$, and $R^1$ may be bonded with each other to form a ring together with a sulfur atom in the formula. $X^1$ represents O or $CH_2$. $A^1$ represents a linear, a branched, or a cyclic divalent hydrocarbon group having 1 to 10 carbon atoms. $B^1$ represents an alkylene group having 1 to 10 carbon atoms or an arylene group having 6 to 18 carbon atoms wherein these groups may contain an ether oxygen atom. $k^1$ represents an integer of 0 or 1.

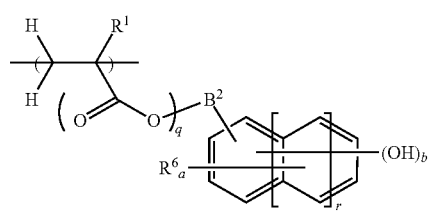

(3)

wherein, "q" represents 0 or 1. "r" represents an integer of 0 to 2. $R^5$ represents any of a hydrogen atom, a fluorine atom, a methyl group, and a trifluoromethyl group; and each $R^6$ independently represents a hydrogen atom or an alkyl group having 1 to 6 carbon atoms. $B^2$ represents a single bond or an alkylene group having 1 to 10 carbon atoms and optionally containing an ether bond. "a" represents an integer satisfying a≤5+2r−b. "b" represents an integer of 1 to 3.

Here, "a" represents an integer satisfying a=5+2r−b; and in the case that all of $R^6$ are hydrogen atoms, the "a" is an integer satisfying a=5+2r−b, while in the case that all of $R^6$ are the alkyl groups having 1 to 6 carbon atoms, the "a" is an integer of 0 to 3.

Preferable specific example of the repeating unit shown by the general formula (2) includes the followings,

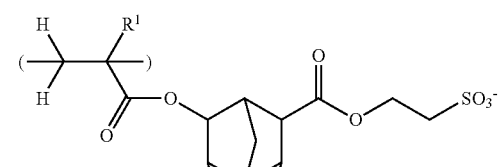

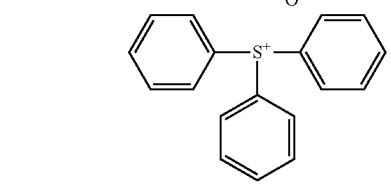

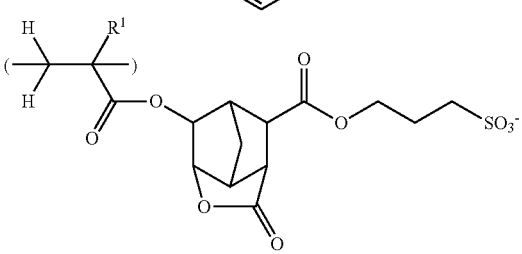

-continued

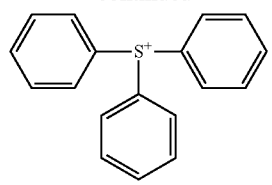

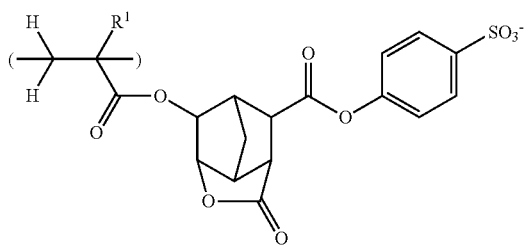

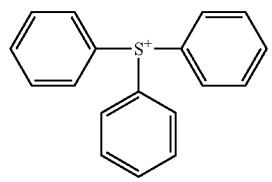

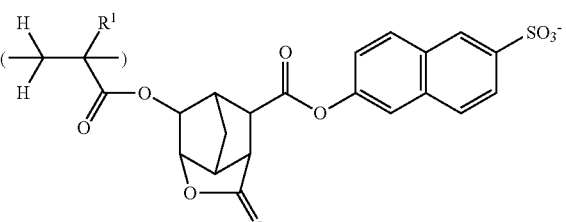

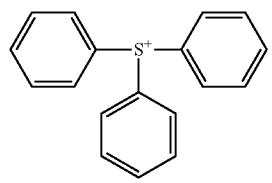

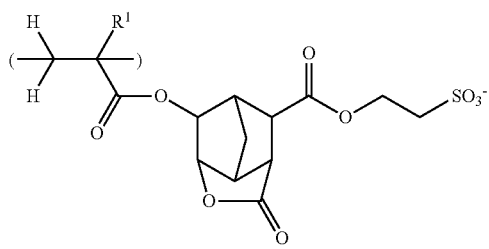

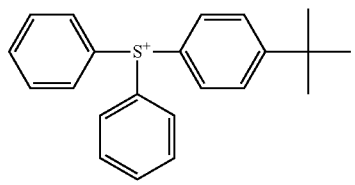

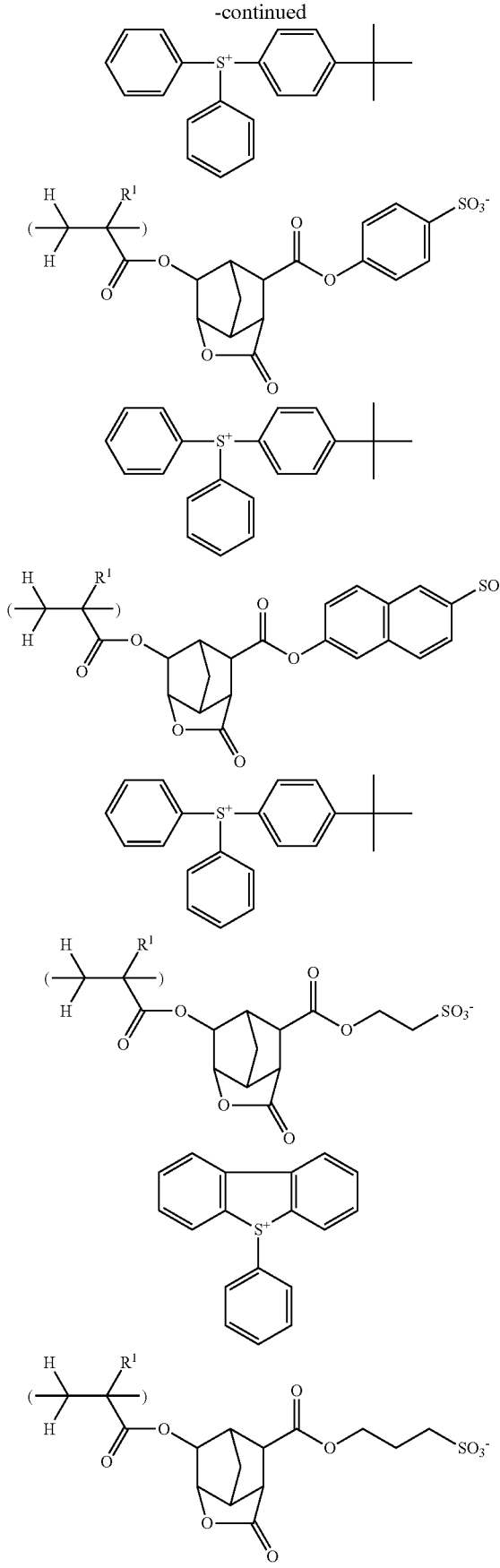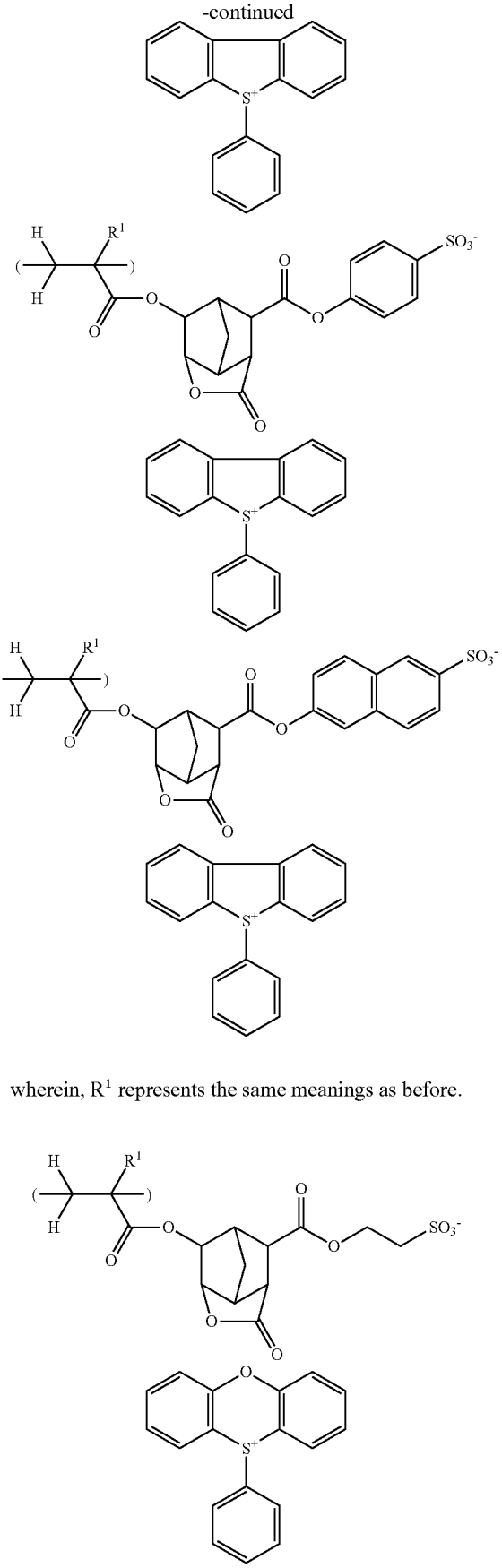
wherein, R[1] represents the same meanings as before.

31
-continued
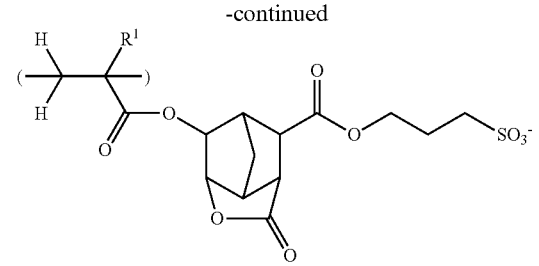
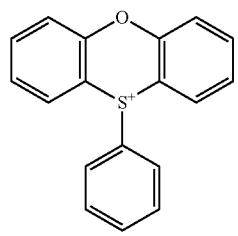
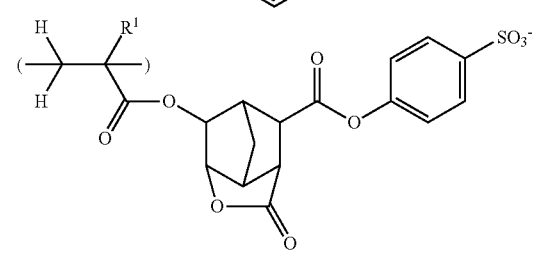
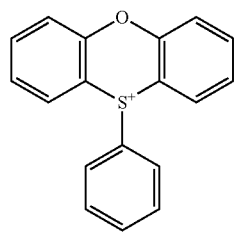
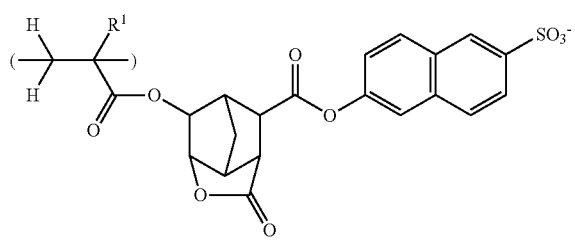
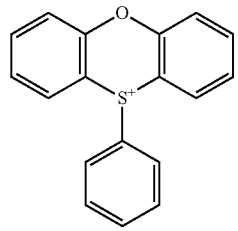 [SMILES: c1ccc([S+]2c3ccccc3Oc3ccccc32)cc1]
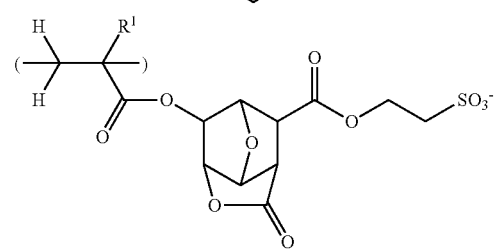
32
-continued
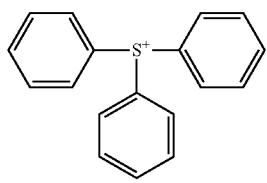
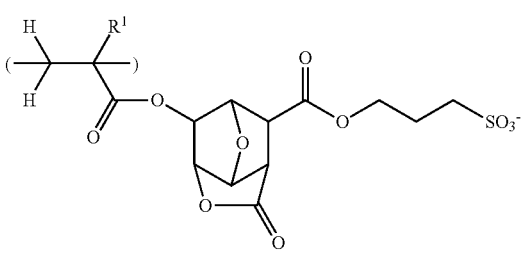
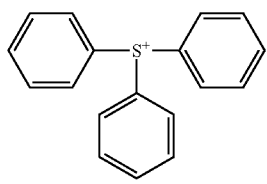
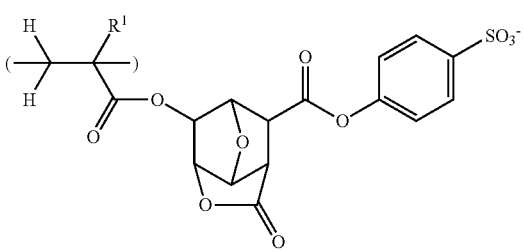
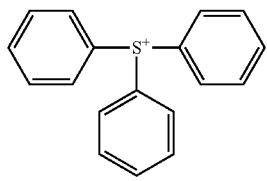
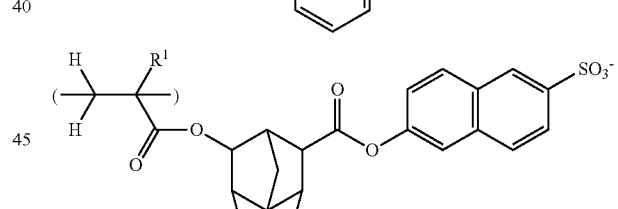
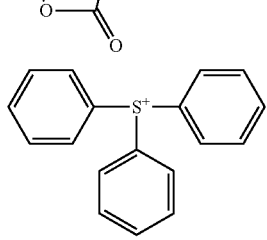
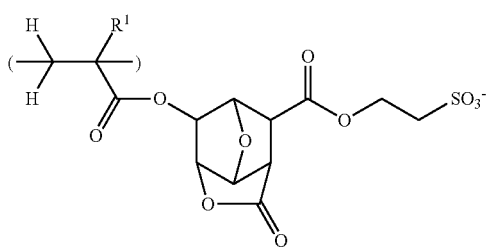

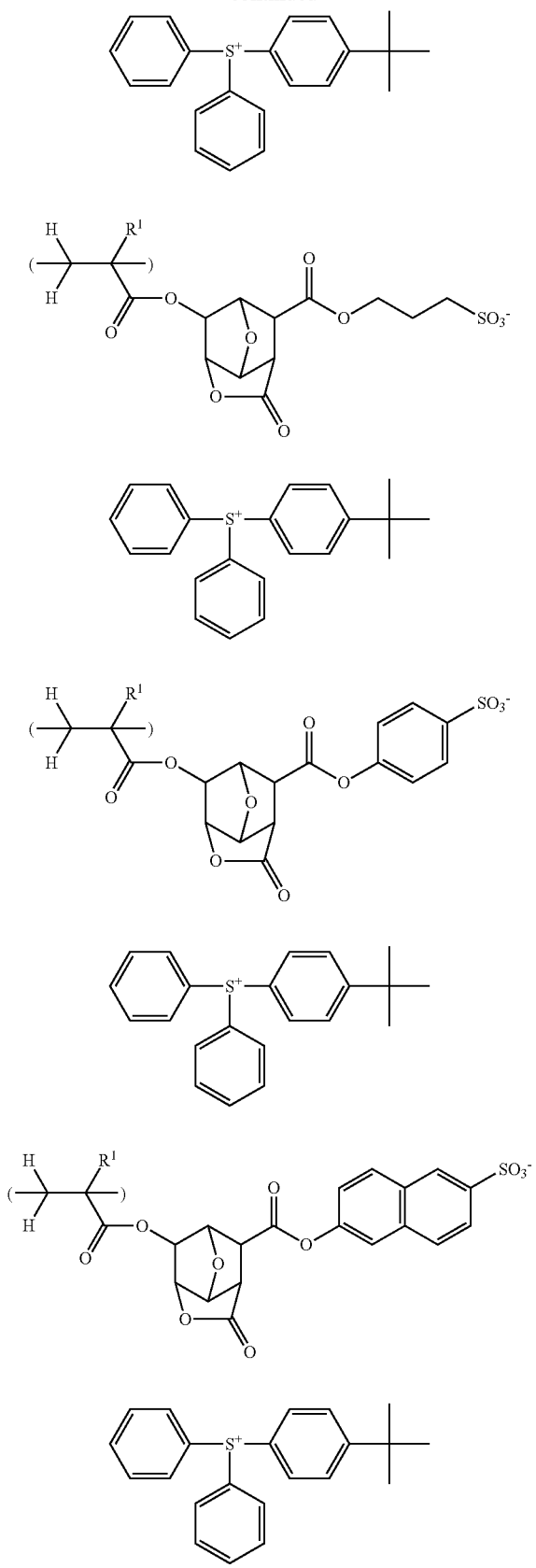
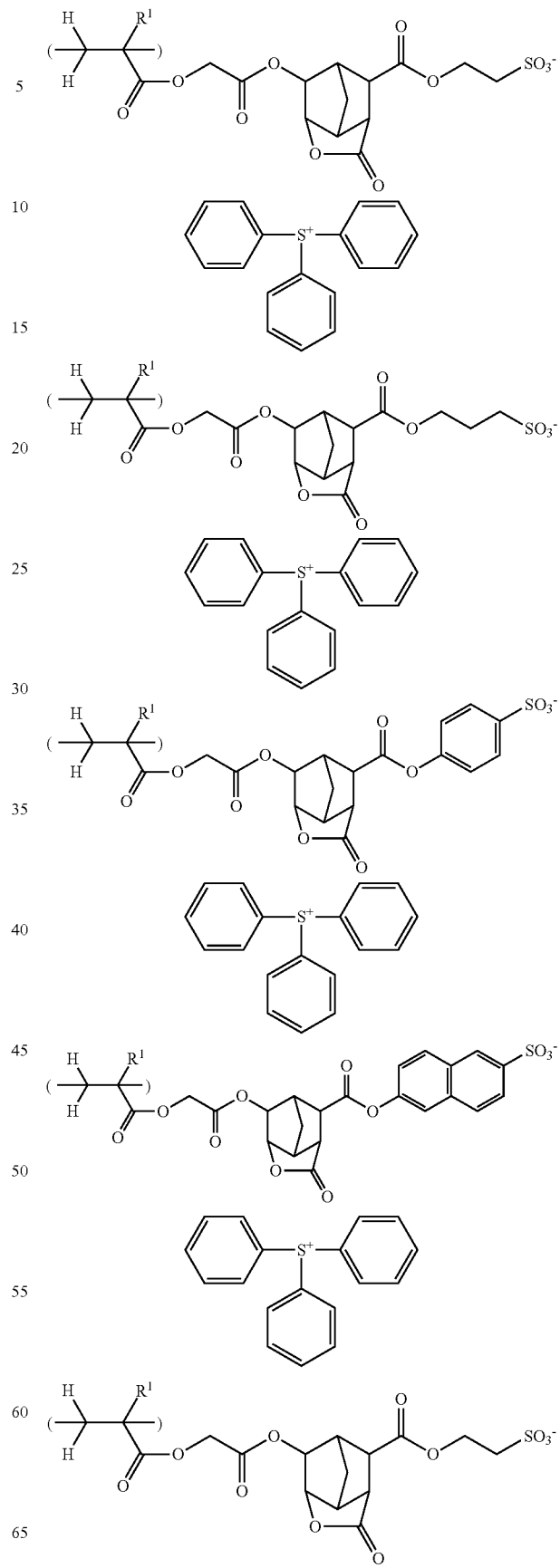
wherein, R¹ represents the same meanings as before.

35
-continued
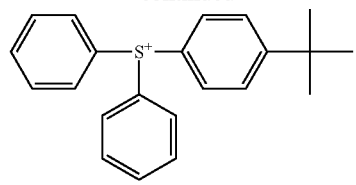
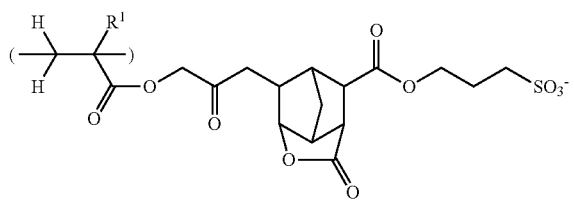
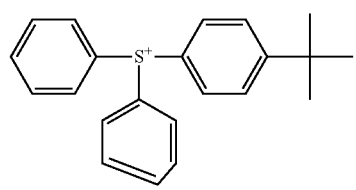
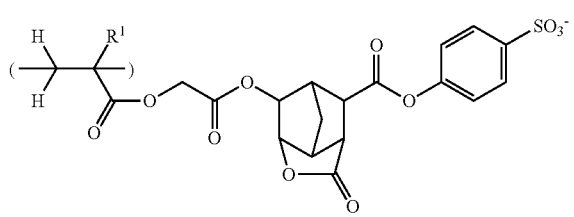
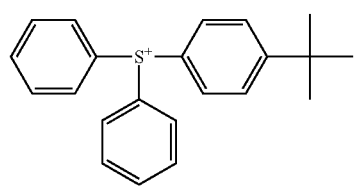
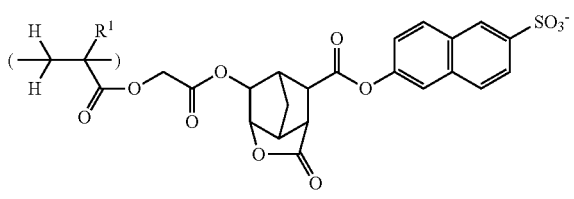
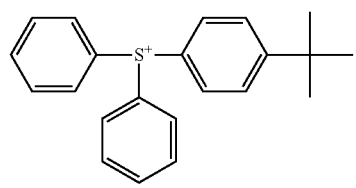
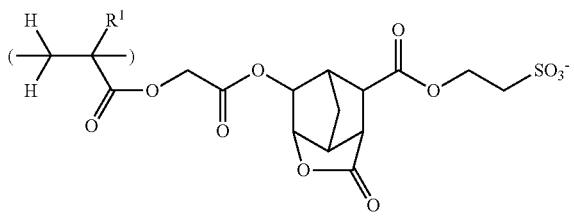
36
-continued
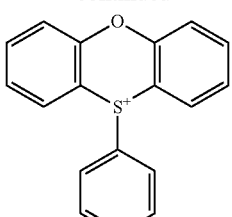
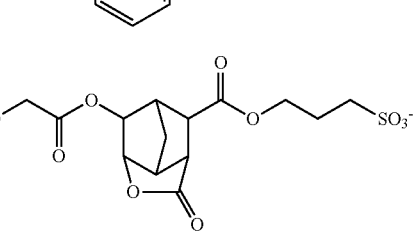
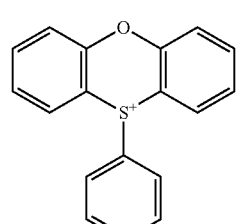
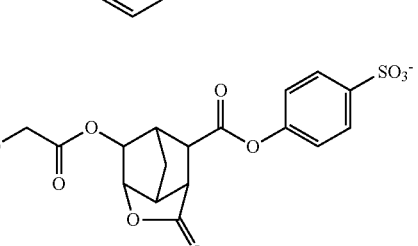
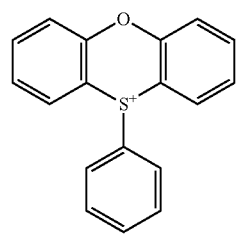
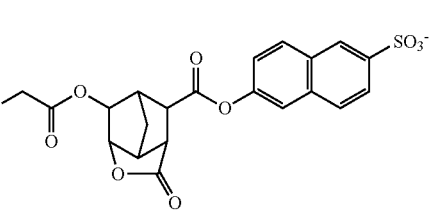
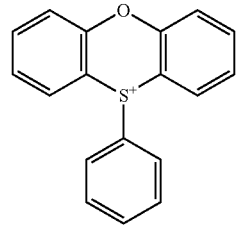
wherein, $R^1$ represents the same meanings as before.

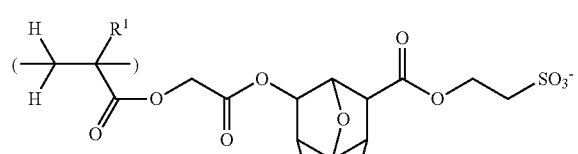
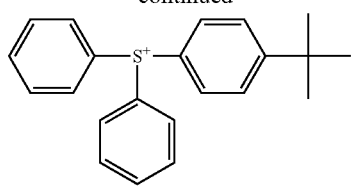
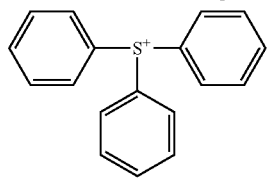
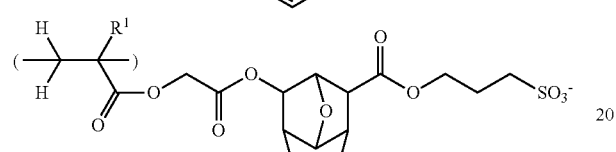
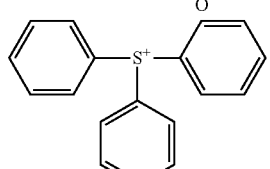
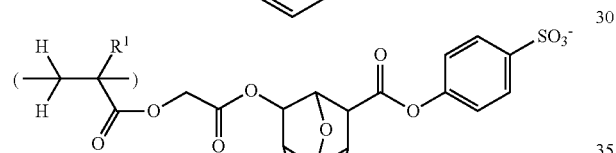
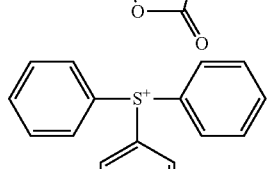
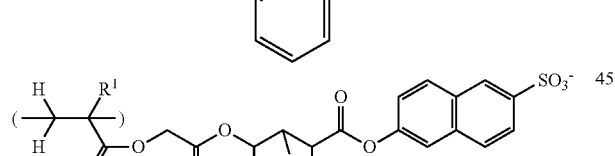
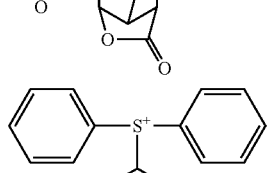
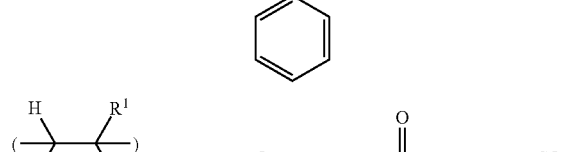
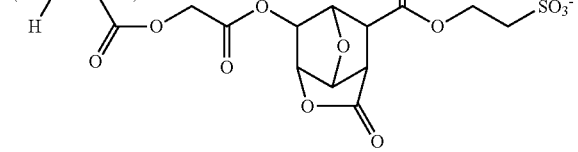

-continued

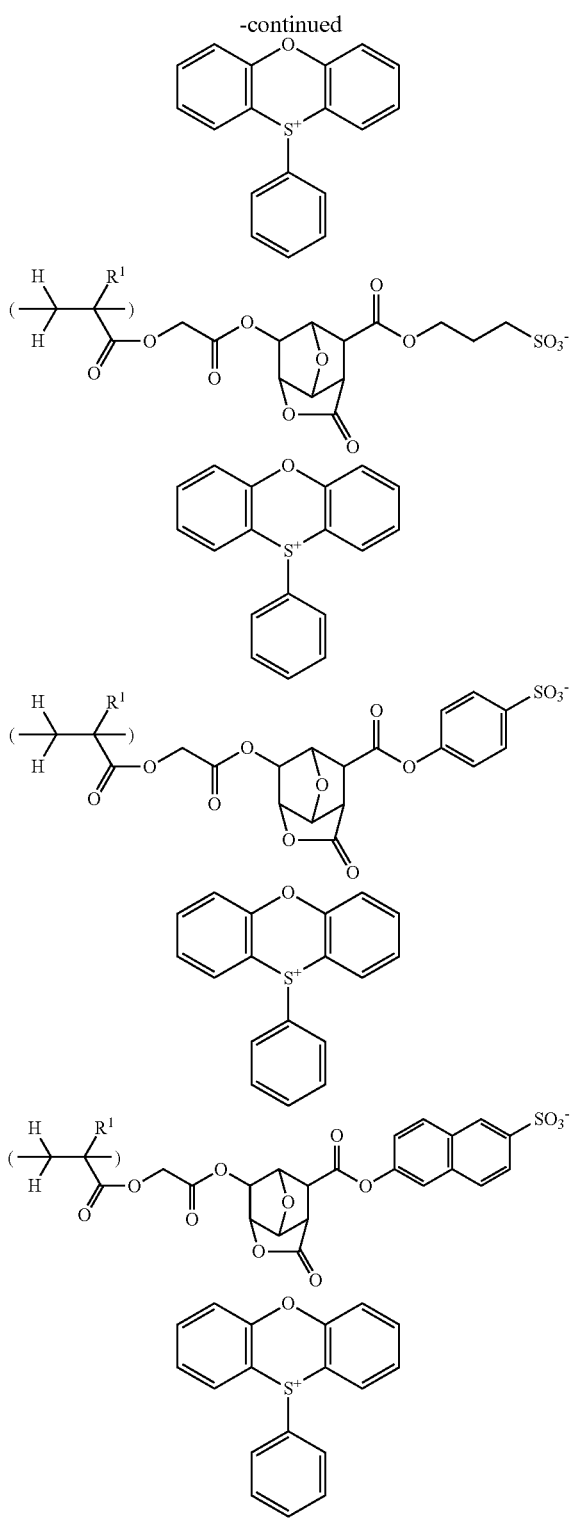

wherein, R¹ represents the same meanings as before.

The polymer of the present invention has a lactone skeleton as the repeating unit to generate an acid by photo-exposure; and thus, it shows good solubility into a solvent and does not impair an adhesion property with a substrate.

The polymer of the present invention contains further a repeating unit shown by the general formula (3) as the unit to provide the polymer with an adhesion property with a substrate by having a polarity within its molecular structure. The polymer like this is effective for preparation of a resist composition especially for EB and EUV.

Of the repeating units shown by the general formula (3), a repeating unit not having a linker (—CO—O—B²—) is the unit derived from a monomer having a vinyl group substituted or unsubstituted at its 1-position that is bonded to an aromatic ring substituted with a hydroxyl group, as represented by a hydroxyl styrene unit and the like; and preferable specific example thereof includes units derived from 3-hydroxy styrene, 4-hydroxy styrene, 5-hydroxy-2-vinyl naphthalene, and 6-hydroxy-2-vinyl naphthalene.

A repeating unit having the linker (—CO—O—B²—) is the unit derived from a vinyl monomer substituted with a carbonyl group, as represented by a (meth)acrylate ester.

Specific example of the repeating unit having the linker (—CO—O—B²—) shown by the general formula (3) includes the followings.

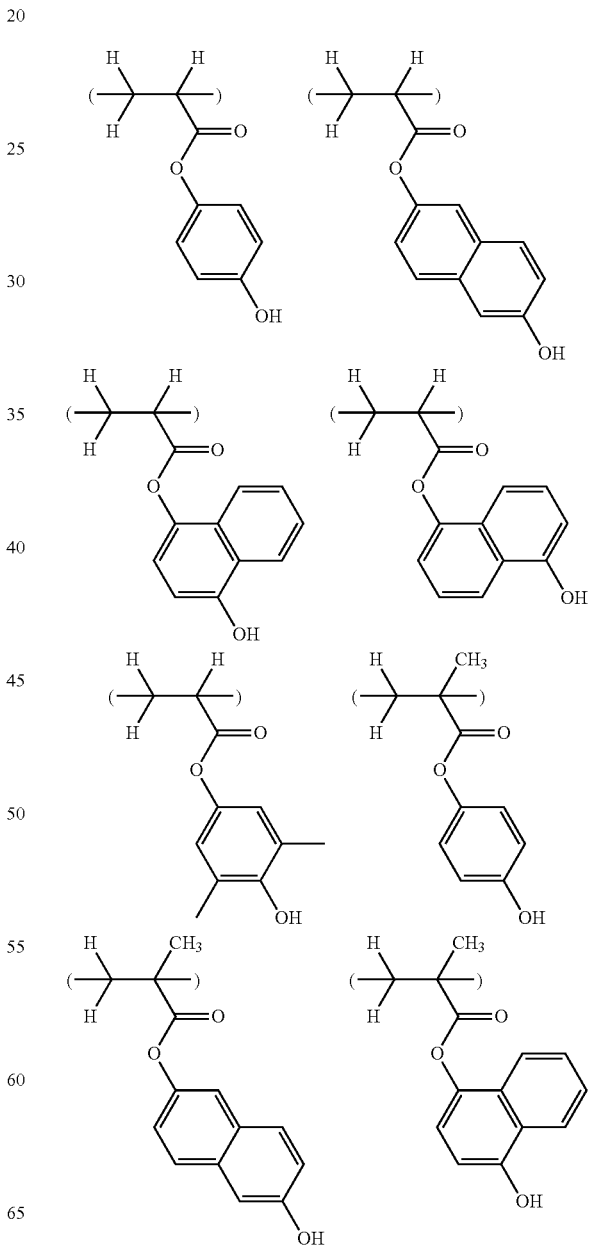

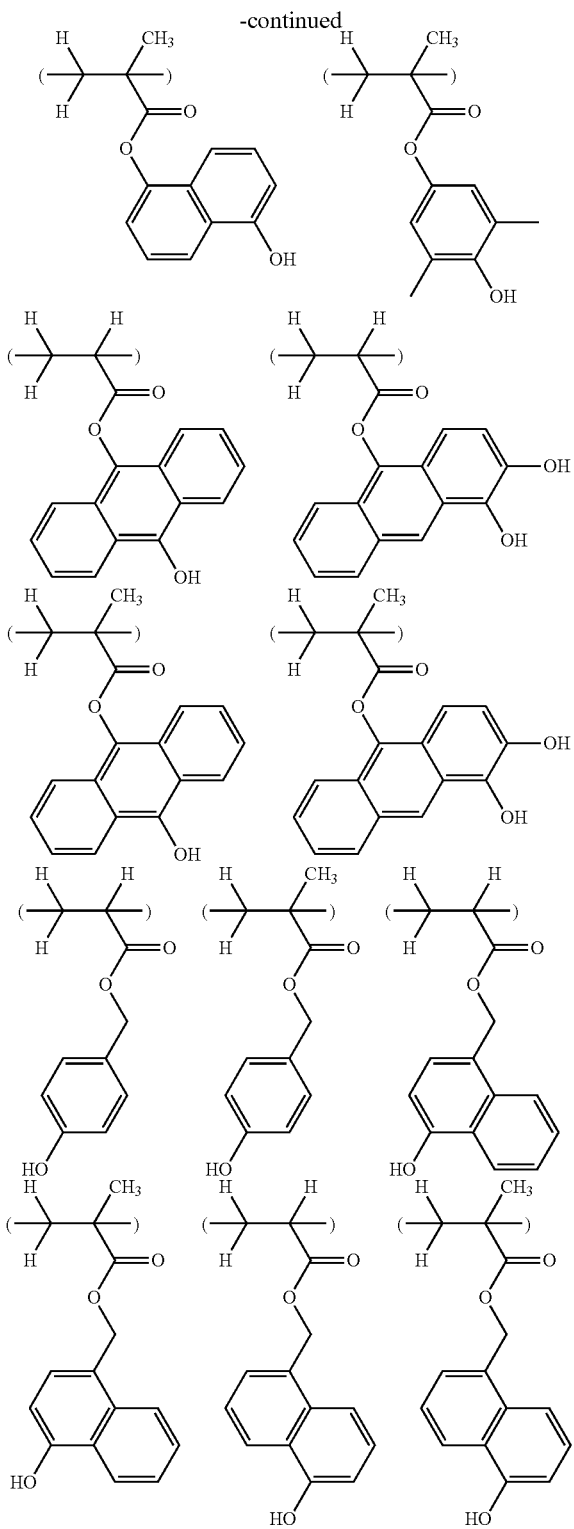

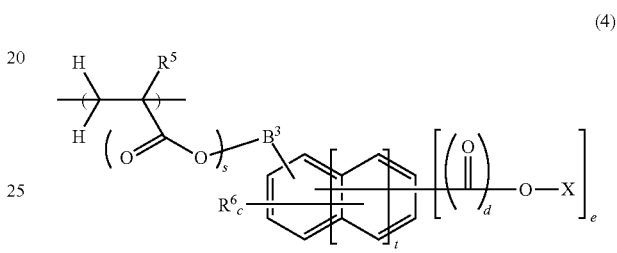

The unit that provides the polymer with an adhesion property, as shown by the general formula (3), may be contained in the polymer singly or as a combination of a plurality of the unit, wherein content of the unit introduced thereto is in the range of 30 to 80% by mol relative to totality of the repeating units of the polymer of the present invention. Meanwhile, in the case that a unit shown by the general formulae (5) and/or (6) that provides the polymer used in the present invention, which will be explained later, with a further higher etching resistance is used, if the unit contains a phenolic hydroxyl group as the substituent group, the foregoing range includes this ((5) and/or (6)) ratio.

The polymer of the present invention gives a property that a photo-exposed part is soluble in an aqueous alkaline solution as a positive resist; and thus, it is preferable that a unit having an acidic functional group protected with an acid-labile group (a unit protected with an acid-labile group and becoming alkaline-soluble by action of an acid) be contained in the polymer. As the most preferable unit, which can be contained in the polymer of the present invention, protected with an acid-labile group and becoming alkaline-soluble by action of an acid, a repeating unit shown by the following general formula (4) may be mentioned, wherein, "s" represents 0 or 1. "t" represents an integer of 0 to 2. $R^5$ and $R^6$ represent the same meanings as before. $B^3$ represents a single bond or an alkylene group having 1 to 10 carbon atoms and optionally containing an ether bond. "c" represents an integer satisfying $c \leq 5+2t-e$. "d" represents 0 or 1 and "e" represents an integer of 1 to 3. X represents an acid-labile group when "e" is 1; and a hydrogen atom or an acid-labile group when "e" is 2 or more, while at least one of X is an acid-labile group.

Meanwhile, "c" represents an integer satisfying $c \leq 5+2t-e$; and in the case that all of $R^6$ are hydrogen atoms, the "c" is an integer satisfying $c=5+2t-e$, while in the case that all of $R^6$ are the alkyl groups having 1 to 6 carbon atoms, the "c" is an integer of 0 to 3.

The general formula (4) has a chemical structure as described below; at least one of the phenolic hydroxyl group substituted on the aromatic ring of the unit shown by the general formula (3) is protected by an acid-labile group, or the phenolic hydroxyl group is substituted with a carboxyl group, which is protected by an acid-labile group; and as to the acid-labile group, any of the group that is capable of giving an acid group by elimination by an acid and has been used in many heretofore known chemically amplified resist composition can be basically used.

In any case of the phenolic hydroxyl group and the carboxyl group, protection by a tertiary alkyl group as a choice of the acid-labile group is particularly preferable because a pattern having small edge roughness (phenomenon to give an irregular edge pattern profile) in a thin resist film with the film thickness of 10 to 100 nm, for example even in the case of a fine pattern with the line width of 45 nm or less is formed. In addition, the tertiary alkyl group having 4 to 18 carbon atoms is preferable because a synthesized monomer for polymerization is obtained by distillation. Further, an alkyl substituent of the tertiary carbon in the tertiary alkyl group may be a linear, a branched, or a cyclic alkyl group having 1 to 15 carbon atoms optionally partially containing an oxygen-containing functional group such as an ether bond and a carbonyl group, wherein the alkyl groups substituted on the tertiary carbon may be bonded with each other to form a ring.

Specific example of the preferable alkyl substituent includes a methyl group, an ethyl group, a propyl group, an adamantly group, a norbornyl group, a tetrahydrofurane-2-yl group, a 7-oxanorbornane-2-yl group, a cyclopentyl group, a 2-tetrahydrofuryl group, a tricyclo[5.2.1.0$^{2,6}$]decyl group, a 8-ethyl-8-tricyclo[5.2.1.0$^{2,6}$]decyl group, a 3-methyl-3-tetracyclo[4.4.0.1$^{2,5}$,1$^{7,10}$]dodecyl group, a tetracyclo[4.4.0.1$^{2,5}$,1$^{7,10}$]dodecyl group, and a 3-oxo-1-cyclohexyl group. Specific example of the tertiary alkyl group includes a t-butyl group, a t-pentyl group, a 1-ethyl-1-methylpropyl group, a 1,1-diethylpropyl group, a 1,1,2-trimethylpropyl group, a 1-adamantyl-1-methylethyl group, a 1-methyl-1-(2-norbornyl)ethyl group, a 1-methyl-1-(tetrahydrofurane-2-yl) ethyl group, a 1-methyl-1-(7-oxanorbornane-2-yl)ethyl group, a 1-methylcyclopentyl group, a 1-ethylcyclopentyl group, a 1-propylcyclopentyl group, a 1-cyclopentylcyclopentyl group, a 1-cyclohexylcyclopentyl group, a 1-(2-tetrahydrofuryl)cyclopentyl group, a 1-(7-oxanorbornane-2-yl) cyclopentyl group, a 1-methylcyclohexyl group, a 1-ethylcyclohexyl group, a 1-cyclopentylcyclohexyl group, a 1-cyclohexylcyclohexyl group, a 2-methyl-2-norbornyl group, a 2-ethyl-2-norbornyl group, a 8-methyl-8-tricyclo [5.2.1.0$^{2,6}$]decyl group, a 8-ethyl-8-tricyclo[5.2.1.0$^{2,6}$]decyl group, a 3-methyl-3-tetracyclo[4.4.0.1$^{2,5}$,1$^{7,10}$]dodecyl group, a 3-ethyl-3-tetracyclo[4.4.0.1$^{2,5}$,1$^{7,10}$]dodecyl group, a 2-methyl-2-adamantyl group, a 2-ethyl-2-adamantyl group, a 1-methyl-3-oxo-1-cyclohexyl group, a 1-methyl-1-(tetrahydrofurane-2-yl)ethyl group, a 5-hydroxy-2-methyl-2-adamantyl group, and a 5-hydroxy-2-ethyl-2-adamantyl group; but the group not limited to them.

An acetal group shown by the following general formula (20) is often used as the acid-labile group,

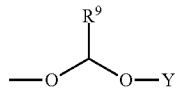

(20)

wherein, R$^9$ represents a hydrogen atom, or a linear, a branched, or a cyclic alkyl group having 1 to 10 carbon atoms, and Y represents a linear, a branched, or a cyclic alkyl group having 1 to 30 carbon atoms, whereby selection thereof is useful as the acid-labile group stably giving a pattern whose interface with a substrate is relatively rectangular. Especially in order to obtain a further higher resolution, it is preferable that the group contain a polycyclic alkyl group having 7 to 30 carbon atoms. In the case that Y contains a polycyclic alkyl group, it is preferable that a bond be formed between the acetal oxygen atom and the secondary carbon atom that constitutes the polycyclic ring structure. This is because, if the bond is formed on the tertiary carbon atom of the ring structure, a polymer becomes unstable, thereby leading to poor storage property as a resist composition and causing resolution deterioration in a certain case. On the contrary, if Y is bonded on the primary carbon atom via a linear alkyl group having one or more carbon atoms, a glass transition temperature (Tg) of the polymer is lowered, thereby causing a poor profile of a resist pattern by baking after development in a certain case.

Specific example of the formula (20) includes the followings,

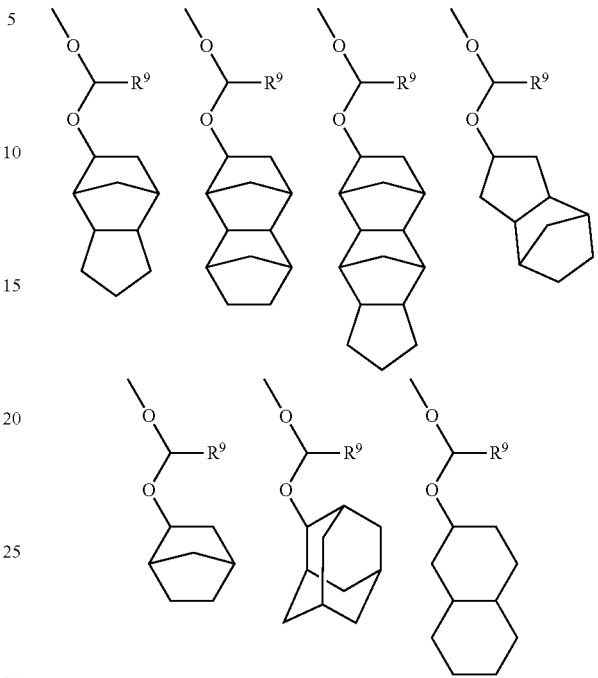

wherein, R$^9$ represents the same meanings as before.

Meanwhile, R$^9$ represents a hydrogen atom, or a linear, a branched, or a cyclic alkyl group having 1 to 10 carbon atoms, and is chosen appropriately in accordance with sensitivity design of the acid-decomposing group to an acid. For example, if the design is made to decompose by a strong acid while securing a comparatively high stability, a hydrogen atom is chosen; if the design is made to be highly sensitive to the pH change by using a comparatively high reactivity, a linear alkyl group is chosen. If the design is made to dispose a comparatively bulky alkyl group at the terminal as mentioned above thereby intending a large solubility change by decomposition, the carbon atom of R$^9$ bonded to the acetal carbon atom is preferably a secondary carbon atom, though depending on a combination of an acid generator and a basic compound contained in the resist composition. Illustrative example of R$^9$ bonded to the acetal carbon atom by the secondary carbon atom includes an isopropyl group, a sec-butyl group, a cyclopentyl group, and a cyclohexyl group.

As to the choice of other acid-labile groups, bonding of the group (—CH$_2$COO-tert-alkyl) to the phenolic hydroxyl group may be chosen. The same tertiary alkyl group used in protection of the phenolic hydroxyl group as mentioned above may also be used in this case.

The unit, shown by the general formula (4), which is protected by an acid-labile group and becomes alkaline-soluble by action of an acid may be used singly or in a combination of a plurality of the unit, with the amount thereof being preferably 5 to 45% by mol relative to totality of the repeating units in the polymer.

The polymer of the present invention can contain further a repeating unit shown by the following formulae (5) and/or (6) as the main constituting units of the polymer,

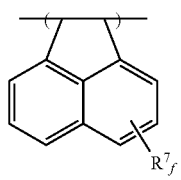

(5)

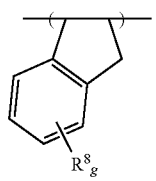

(6)

wherein, "f" represents an integer of 0 to 6, and each $R^7$ independently represents any of a hydrogen atom, an alkyl group or a primary or a secondary alkoxy group having 1 to 6 carbon atoms and optionally substituted with a halogen atom, and an alkylcarbonyloxy group having 1 to 7 carbon atoms and optionally substituted with a halogen atom. "g" represents an integer of 0 to 4; and each $R^8$ independently represents any of a hydrogen atom, an alkyl group or a primary or a secondary alkoxy group having 1 to 6 carbon atoms and optionally substituted with a halogen atom, and an alkylcarbonyloxy group having 1 to 7 carbon atoms and optionally substituted with a halogen atom.

When these repeating units (at least one or more of the repeating units shown by the general formulae (5) and (6)) are used as the constituting components of the polymer, in addition to the etching resistance due to the aromatic ring, an effect of enhancing resistance to an electron beam during the time of etching and pattern inspection can be increased due to the ring structures added to the polymer's main chain.

The unit that provides the main chain with a ring structure thereby increasing etching resistance, as shown by the general formula (5) or (6), may be used singly or in a combination of a plurality of the unit, with the amount thereof being preferably 5% by mol or more relative to totality of the monomer units to constitute the polymer in view of obtaining the effect to increase etching resistance. In the case that the unit shown by the general formula (5) or (6) gives rise to the adhesion property with a substrate by a polarity given by the action of a functional group contained in the general formula (5) or (6), or the unit thereof has a substituent protected by the acid-labile group whereby becoming alkaline-soluble by the action of an acid, the introduction amount of the unit is added to the respective foregoing preferable ranges; and in the case that the functional group is not contained therein or the functional group is not either of them, the amount thereof is preferably 30% by mol or lower. In the case that the functional group is not contained therein or the functional group is not either of them, if the introduction amount is 30% by mol or lower, this is preferable because there is no fear of causing a development defect.

In the case that the polymer of the present invention is used as a base polymer of a chemically amplified resist composition, amount of the repeating unit of the polymer generating an acid by photo-exposure as shown by the general formula (2) is preferably 0.1 to 15% by mol, or more preferably 1 to 10% by mol, relative to totality of the monomer units of the polymer. If amount of the repeating unit shown by the general formula (2) is 0.1% by mol or more, this is preferable because there is no fear of impairing adhesion with a substrate or of not obtaining pattern due to insufficient amount of an acid generated by photo-exposure. If amount of the repeating unit shown by the general formula (2) is 15% by mol or lower, this is preferable because there is no fear of not lowering solubility of the polymer into a solvent thereby not obtaining a resist composition.

In the polymer used in the chemically amplified resist composition of the present invention, if main constituting units shown by the general formulae (2) and (3) and additionally introducible units shown by the general formulae (4) to (6) are contained therein with the amount of preferably 60% by mol or more relative to totality of the monomer units that constitute the polymer, characteristics of the chemically amplified resist composition of the present invention can be obtained for sure, wherein the amount thereof is more preferably 70% by mol or more, or still more preferably 85% by mol or more.

Further, if the polymer is wholly composed of the repeating units selected from (2) to (6), both high etching resistance and excellent resolution can be obtained. As to repeating units other than (2) to (6), a (meth)acrylate ester unit protected with a usually used acid-labile group and a (meth)acrylate ester unit having an adhesive group such as a lactone structure, as shown in Japanese Patent Laid-Open (kokai) No. 2008-133448, may be used. Fine tuning of characteristics of the resist film may be done by these other repeating units; but these units may not be contained therein.

The polymer of the present invention can be obtained by copolymerizing respective monomers by a conventional method with combined protection and deprotection reactions as appropriate. The copolymerization reaction is not particularly restricted, though radical polymerization and anionic polymerization are preferable. These methods may be referred to International Patent Laid-Open Publication No. 2006/121096, Japanese Patent Laid-Open (kokai) No. 2008-102383, Japanese Patent Laid-Open (kokai) No. 2008-304590, and Japanese Patent (kokai) Publication No. 2004-115630.

Molecular weight of the polymer used as a base polymer of the chemically amplified resist composition is preferably 2,000 to 50,000, or more preferably 3,000 to 20,000, as the weight-average molecular weight measured by a general GPC (gel-permeation chromatography), relative to the polystyrene standard sample. If the weight-average molecular weight is 2,000 or more, there are no fears of decrease in resolution with a round-head pattern and deterioration of the line edge roughness, the phenomena known in the past. On the other hand, if the molecular weight is larger than necessary, the line edge roughness tends to increase though depending on the pattern resolved; and thus, the molecular weight is controlled at preferably 50,000 or less, or at 20,000 or less especially in the case that a pattern with the line width of 100 nm or less is formed.

In the GPC measurement, tetrahydrofurane (THF) is generally used as the solvent for it, but in the present invention there is a case that dissolution in THF is difficult; in this case, measurement may be carried out in a solvent of dimethyl formamide (DMF) added with 100 mM (mol/L) or less of lithium bromide.

In addition, in the polymer used in the chemically amplified resist composition of the present invention, molecular weight distribution (Mw/Mn) thereof is preferably in the narrow range of 1.0 to 2.0, in particular 1.0 to 1.8. In the case of narrow range like this, there is no problem of forming a foreign spot on the pattern or deterioration of the pattern profile after development.

The chemically amplified resist composition of the present invention can acquire a basic resist performance by adding a solvent mentioned later; but a basic compound, an acid generator, other polymer, a surfactant, and the like may be added thereinto as necessary.

A basic compound is substantially an indispensable component in the chemically amplified resist composition having an acid-generating unit not bonded to a polymer; but in the resist composition of the present invention, it is also preferable to add a basic compound thereinto in order to obtain a high resolution or to control to a suitable sensitivity. The amount thereof is preferably in the range of 0.01 to 5 parts by mass, in particular 0.05 to 3 parts by mass, relative to 100 parts by mass of the polymer. Many usable basic compounds have been known (Japanese Patent Laid-Open (kokai) No. H09-325497, Japanese Patent Laid-Open (kokai) No. 2008-133448, Japanese Patent Laid-Open (kokai) No. 2000-159758, Japanese Patent Laid-Open (kokai) No. 2007-182488, and International Patent Laid-Open Publication No. 2006/121096), including an aliphatic amine such as a primary, a secondary, and a tertiary amine, a mixed amine, an aromatic amine, a heterocyclic amine, a nitrogen-containing compound having a carboxy group, a nitrogen-containing compound having a sulfonyl group, a nitrogen-containing compound having a hydroxyl group, a nitrogen-containing compound having a hydroxyphenyl group, an alcoholic nitrogen-containing compound, an amide, an imide, a carbamate, and an ammonium salt. Many specific examples of them are shown in Japanese Patent Laid-Open (kokai) No. 2008-133448; and basically, all of them can be used, and in addition, two or more of the basic compounds may be selected and mixed to be used as a mixture.

Especially preferable basic compound to be blended includes tris(2-(methoxymethoxy)ethyl)amine-N-oxide, a morpholine derivative, and an imidazole derivative.

In the case that patterning is made on a substrate easily causing a phenomenon that dissolution of a positive pattern in the substrate interface is difficult during patterning process, namely a phenomenon of causing a so-called footing profile (this also occurs on a substrate having a surface of a chromium compound), the pattern profile may be improved by using an amine compound or an amine oxide compound having a carboxyl group but not having a hydrogen atom covalently bonded to a nitrogen atom of a basic center (excluding an amine and an amine oxide whose nitrogen atom is included in an aromatic ring structure).

The amine compound or the amine oxide compound having a carboxyl group but not having a hydrogen atom covalently bonded to a nitrogen atom of a basic center as mentioned above is preferably the amine compound or the amine oxide compound having at least a carboxyl group and not having a hydrogen atom covalently bonded to a nitrogen atom of a basic center as shown in the following general formulae (21) to (23), but not limited to them,

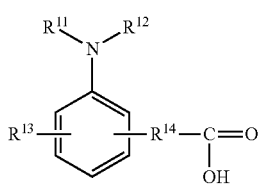

(21)

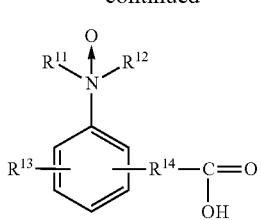

(22)

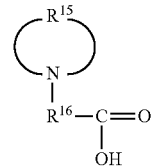

(23)

wherein, each of $R^{11}$ and $R^{12}$ represents any of a linear, a branched, or a cyclic alkyl group having 1 to 20 carbon atoms, an aryl group having 6 to 20 carbon atoms, an aralkyl group having 7 to 20 carbon atoms, a hydroxyalkyl group having 2 to 10 carbon atoms, an alkoxy alkyl group having 2 to 10 carbon atoms, an acyloxy alkyl group having 2 to 10 carbon atoms, and an alkyl thioalkyl group having 1 to 10 carbon atoms. $R^{11}$ and $R^{12}$ may be bonded with each other to form a ring structure together with a nitrogen atom to which these groups are bonded. $R^{13}$ represents any of a hydrogen atom, a linear, a branched, or a cyclic alkyl group having 1 to 20 carbon atoms, an aryl group having 6 to 20 carbon atoms, an aralkyl group having 7 to 20 carbon atoms, a hydroxyalkyl group having 1 to 10 carbon atoms, an alkoxy alkyl group having 2 to 10 carbon atoms, an acyloxy alkyl group having 2 to 11 carbon atoms, an alkyl thioalkyl group having 1 to 11 carbon atoms, and a halogen group. $R^{14}$ represents a single bond, a linear, a branched, or a cyclic alkylene group having 1 to 20 carbon atoms, or an arylene group having 6 to 20 carbon atoms. $R^{15}$ represents an optionally substituted linear or branched alkylene group having 2 to 20 carbon atoms and optionally containing one or a plurality of the groups selected from a carbonyl group, an ether group, an ester group, and a sulfide group between a carbon-carbon bond of the alkylene group. $R^{16}$ represents a linear, a branched, or a cyclic alkylene group having 1 to 20 carbon atoms or an arylene group having 6 to 20 carbon atoms.

Specific example of the aryl group having 6 to 20 carbon atoms includes a phenyl group, a naphthyl group, an anthryl group, a phenanthryl group, a pyrenyl group, a naphthacenyl group, and a fluorenyl group. Specific example of the linear, the branched, or the cyclic alkyl group having 1 to 20 carbon atoms includes a methyl group, an ethyl group, a propyl group, an isopropyl group, a butyl group, an isobutyl group, a t-butyl group, a pentyl group, a hexyl group, a decyl group, a cyclopentyl group, a cyclohexyl group, and a decahydronaphtharenyl group. Specific example of the aralkyl group having 7 to 20 carbon atoms includes a benzyl group, a phenethyl group, a phenylpropyl group, a naphthylmethyl group, a naphthylethyl group, and an anthracenylmethyl group. Specific example of the hydroxyalkyl group having 1 to 10 carbon atoms includes a hydroxymethyl group, a hydroxyethyl group, and a hydroxypropyl group. Specific example of the alkoxy alkyl group having 2 to 10 carbon atoms includes a methoxymethyl group, a 2-methoxyethyl group, an ethoxymethyl group, a 2-ethoxyethyl group, a propoxymethyl group, a 2-propoxyethyl group, a butoxymethyl group, a 2-butoxyethyl group, an amyloxy methyl group, a 2-amyloxyethyl group, a cyclohexyloxymethyl group, a 2-cyclohexyloxyethyl group, a cyclopentyloxymethyl group, and a 2-cyclopentyloxyethyl group including isomers in its alkyl group. Specific example of the acyloxy alkyl group having 2 to 11 carbon atoms includes a formyloxy methyl group, an acetoxy methyl group, a propionyloxy methyl group, a butyryloxy methyl group, a pivaloyloxy methyl group, a cyclohexanecarbonyloxy methyl group, and a decanoyloxy methyl group. Specific example of the alkyl thioalkyl group having 1 to 11 carbon atoms includes a methyl thiomethyl group, an ethyl thiomethyl group, a propyl thiomethyl group, an isopropyl thiomethyl group, a butyl thiomethyl group, an isobutyl thiomethyl group, a t-butyl thiomethyl group, a t-amyl thiomethyl group, a decyl thiomethyl group, and a cyclohexyl thiomethyl group. These groups are not limited to the above-mentioned examples.

Specific examples of the amine compound having a carboxyl group but not having a hydrogen atom covalently bonded to a nitrogen atom of a basic center as shown in the general formula (21) are shown in the followings, though not limited to them.

Namely, specific example thereof includes o-dimethylaminobenzoic acid, p-dimethylaminobenzoic acid, m-dimethylaminobenzoic acid, p-diethylaminobenzoic acid, p-dipropylaminobenzoic acid, p-dibutylaminobenzoic acid, p-dibutylaminobenzoic acid, p-dipentylaminobenzoic acid, p-dihexylaminobenzoic acid, p-diethanolaminobenzoic acid, p-diisopropanolaminobenzoic acid, p-dimethanolaminobenzoic acid, 2-methyl-4-diethylaminobenzoic acid, 2-methoxy-4-diethylaminobenzoic acid, 3-dimethylamino-2-naphthalenic acid, 3-diethylamino-2-naphthalenic acid, 2-dimethylamino-5-bromobenzoic acid, 2-dimethylamino-5-chlorobenzoic acid, 2-dimethylamino-5-iodobenzoic acid, 2-dimethylamino-5-hydroxybenzoic acid, 4-dimethylaminophenylacetic acid, 4-dimethylaminophenylpropionic acid, 4-dimethylaminophenylbutyric acid, 4-dimethylaminophenylmalic acid, 4-dimethylaminophenylpyruvic acid, 4-dimethylaminophenyllactic acid, 2-(4-dimethylaminophenyl)benzoic acid, and 2-(4-(dibutylamino)-2-hydroxybenzoyl)benzoic acid.

The amine oxide compounds having a carboxyl group but not having a hydrogen atom covalently bonded to a nitrogen atom of a basic center as shown by the general formula (22) are those obtained by oxidizing the amine compounds specifically exemplified above, though not limited to them.

Specific examples of the amine compound having a carboxyl group but not having a hydrogen atom covalently bonded to a nitrogen atom of a basic center as shown in the general formula (23) are shown in the followings, though not limited to them.

Namely, specific example thereof includes 1-piperidinepropionic acid, 1-piperidinebutyric acid, 1-piperidinemalic acid, 1-piperidinepyruvic acid, and 1-piperidinelactic acid.

The amine oxide compounds shown by the general formula (22) can be synthesized easily by the method disclosed in Japanese Patent Laid-Open (kokai) No. 2008-102383. Specific examples of the amine oxide compounds are described extensively also in Japanese Patent Laid-Open (kokai) No. 2008-102383.

In the chemically amplified resist composition of the present invention, an acid is generated by exposure to a high energy beam owing to the repeating unit shown by the general formula (2) contained in a polymer to be used, and this generated acid is bonded to the polymer thereby having a characteristic of suppressed diffusion; and thus, basically it is not necessary to add other acid generator. However, when higher sensitivity is supplementarily required or improvement in roughness and so on is needed, small amount of other acid generator may be added. However, if excessive amount thereof is added, there is a possibility of losing effect of the acid generator bonded to the polymer of the present invention; and thus, amount of the other acid generator is preferably not more than the mole equivalent based on the structure shown by the general formula (2) contained as the repeating unit in the polymer of the composition, or more preferably a half or less relative to the mole equivalent based on the structure shown by the general formula (2).

Acid generator to be added separately from the polymer of the present invention can be selected appropriately with referring to heretofore known acid generators (many examples thereof are described in International Patent Laid-Open Publication No. 2006/121096, Japanese Patent Laid-Open (kokai) No. 2008-102383, Japanese Patent Laid-Open (kokai) No. 2008-304590, and Japanese Patent Laid-Open (kokai) No. 2004-115630) in accordance with physical properties of the resist composition to be prepared.

Amount thereof to be blended is preferably less than 15 parts by mass, or more preferably 10 parts by mass or less, relative to 100 parts by mass of the polymer, because effect of the acid generator bonded to the polymer of the present invention is impaired if the amount thereof is 15 or more parts by mass. Especially in the case of a acid generator generating a sulfonic acid having a low molecular weight, for example, a sulfonic acid having 6 or less carbon atoms, the amount thereof is preferably 5 or less parts by mass.

In the chemically amplified resist composition of the present invention, a polymer containing the units shown by the general formulae (2) and (3) and preferably containing further a unit selected from the units shown by the general formulae (4) to (6) may be used singly or as a mixture of plurality of them; and in addition, a polymer containing an acid-generating unit having a structure different from the unit shown by the general formula (2), a polymer changeable to alkaline-soluble by an acid though not having an acid-generating unit as shown in the general formula (2), or a polymer that is alkaline-soluble regardless of the reaction with an acid may be contained in the composition. As disclosed in Japanese Patent Laid-Open (kokai) No. 2008-133448, illustrative example of the other polymer includes 1) a poly (meth)acrylic acid derivative, ii) a copolymer of a norbornene derivative and maleic anhydride, iii) a hydrogenated ring-opened metathesis polymer, iv) a copolymer of vinyl ether, maleic anhydride, and a (meth)acrylic acid derivative, and v) a poly(hydroxyl styrene) derivative; these are, in fact, heretofore known polymers for a chemically amplified positive resist that is changeable to alkaline-soluble by an acid. To improve a pattern profile and so on and suppress generation of a residue in development, an alkaline-soluble polymer may be added; for this, many heretofore known polymers used for a chemically amplified negative resist composition may be used. In addition, a fluorine-containing polymer as disclosed in Japanese Patent Laid-Open (kokai) No. 2008-304590 may also be added.

When the polymer of the present invention is used as a mixture with other polymer, the mixing ratio of the polymer of the present invention is preferably 30% or more by mass, or more preferably 50% or more by mass. If the mixing ratio of the polymer of the present invention is 30% or more by mass, this is preferable because there is no fear of a development defect. However, during the time of mixing, it is preferable that the ratio of the unit having an aromatic skeleton relative to entire repeating units of the polymers to be mixed be not 60% or less by mol. Meanwhile, the other polymer mentioned above may be added not only singly but also as a mixture of two or more of them. Performance of the chemically amplified resist composition may be controlled by using a plurality of the polymers.

Into the chemically amplified resist composition of the present invention may be added a surfactant that is usually used to improve coating properties. In the case that a surfactant is used, many surfactants have been known as disclosed in International Patent Laid-Open Publication No. 2006/121096, Japanese Patent Laid-Open (kokai) No. 2008-102383, Japanese Patent Laid-Open (kokai) No. 2008-304590, Japanese Patent Laid-Open (kokai) No. 2004-115630, and Japanese Patent Laid-Open (kokai) No. 2005-8766; and thus, selection thereof may be done with referring to them.

Meanwhile, addition amount of the surfactant is preferably 2 or less parts by mass, more preferably 1 or less part by mass, and 0.01 or more part by mass relative to 100 parts by mass of the base polymer in the chemically amplified resist composition.

To form a pattern by using the chemically amplified resist composition of the present invention, a heretofore known lithography technique may be used. Generally, a resist film is formed by applying the composition onto a substrate to be processed such as a substrate for manufacturing an integrated circuit (Si, $SiO_2$, SiN, SiON, TiN, WSi, BPSG, SOG, organic anti-reflecting film, and so on) and a substrate for manufacturing a mask circuit (Cr, CrO, CrON, MoSi, and so on) by a method such as spin coating so as to make a film thickness of 0.05 to 2.0 μm, which is then followed by pre-baking on a hot plate at 60 to 150° C. for 1 to 10 minutes, or preferably at 80 to 140° C. for 1 to 5 minutes.

Then, by using a mask to form an intended pattern or by a beam exposure, a pattern irradiation is done with a high energy beam such as a deep UV beam, an excimer laser beam, an X-ray, and an electron beam with the exposure dose of 1 to 200 $mJ/cm^2$, or preferably 10 to 100 $mJ/cm^2$. Here, the chemically amplified resist composition of the present invention is especially effective for a pattern irradiation using EUV or an electron beam. Photo-exposure may be done by a usual exposure method, or by an immersion method in which the space between a mask and a resist is immersed. In the latter case, a top coat not soluble in water may also be used.

Thereafter, post-exposure bake (PEB) is done on a hot plate at 60 to 150° C. for 1 to 5 minutes, or preferably at 80 to 140° C. for 1 to 3 minutes. Then, development is done by using an aqueous alkaline developer such as tetramethyl ammonium hydroxide (TMAH) with concentration thereof being 0.1 to 5% by mass, or preferably 2 to 3% by mass, for 0.1 to 3 minutes, or preferably for 0.5 to 2 minutes, with a usually used method such as a dip method, a puddle method, and a spray method to form an intended pattern on a substrate.

Meanwhile, the resist composition of the present invention has especially high etching resistance. The composition is useful when it is used under the condition requiring a little change of pattern line width even if the time to the post-exposure baking after exposure is prolonged. In addition, the composition is particularly useful when it is applied to a substrate to be processed having on its surface a material easily causing pattern peel-off or pattern fall because of poor adhesion of a resist pattern; and thus, it is useful for forming a pattern on a substrate having a film obtained by sputtering a metal chromium; or a chromium compound containing one or more light elements selected from oxygen, nitrogen, and carbon, especially for forming a pattern on a photomask blank.

EXAMPLES

Hereinafter, the present invention will be explained specifically by showing Synthesis Examples, Examples, and Comparative Examples; but the present invention is not restricted by the following Examples. Meanwhile, Me in the following description means a methyl group. Composition ratio of copolymers is expressed by the mole ratio; and weight-average molecular weight (Mw) is shown by the polystyrene-equivalent weight-average molecular weight measured by a gel permeation chromatography (GPC).

Synthesis Example 1

Polymerizable anion-containing sulfonium salts PM-1 to PM-6 of the present invention were synthesized by the prescriptions shown below. Structures of the synthesized sulfonium salts of the present invention (PM-1 to PM-6) and of PM-7 used for Comparative Examples are shown in Table 2.

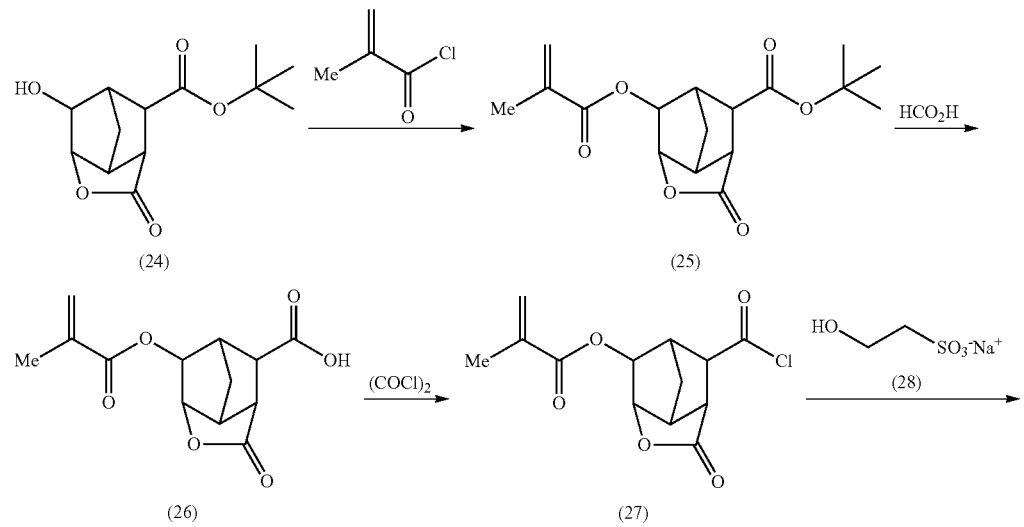

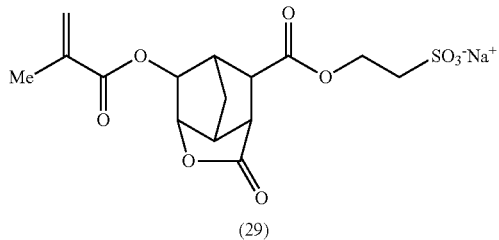

(29)

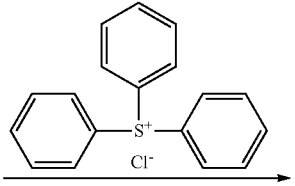

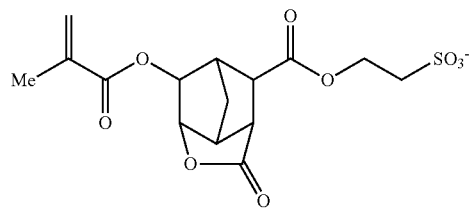

(PM-1)

Synthesis Example 1-1

Synthesis of PM-1

Synthesis Example 1-1-1

Synthesis of 7-Tert-butoxycarbonyl-2-oxohexahydro-3,5-methano-2H-cyclopenta[b]furane-6-yl Methacrylate (25)

Dissolved into 900 mL of acetonitrile were 226.8 g of tert-butyl 6-hydroxy-2-oxohexahydro-3,5-methano-2H-cyclopenta[b]furane-7-carboxylate (24) and 135.2 g of triethylamine. Into this mixture was gradually added 121.1 g of methacryloyl chloride at 20° C. or lower. After the resulting mixture was stirred at room temperature for 3 hours, 300 g of water was added into it and usual work-up was carried out. Recrystallization was made from ethyl acetate to give 202.2 g of the intended product (Yield 70%).

Synthesis Example 1-1-2

Synthesis of 6-Methacryloyloxy-2-oxohexahydro-3,5-methano-2H-cyclopenta[b]furane-7-carboxylic Acid (26)

Dissolved into 810 g of formic acid was 202.2 g of the methacrylate ester (25) obtained in Synthesis Example 1-1-1; and then, the resulting mixture was stirred at 25° C. for 16 hours. After formic acid was removed by distillation under reduced pressure, recrystallization was made from ethyl acetate to give 135.1 g of the intended product (Yield 81%).

Synthesis Example 1-1-3

Synthesis of 7-Chlorocarbonyl-2-oxohexahydro-3,5-methano-2H-cyclopenta[b]furane-6-yl Methacrylate (27)

Suspended into 135 mL of toluene was 18.0 g of the carboxylic acid (26) obtained in Synthesis Example 1-1-2, and then into the resulting suspension was gradually added 10.3 g of oxalyl chloride at 80° C. After this mixture was stirred for 4 hours, toluene was removed by distillation under reduced pressure to obtain the intended product. The obtained acid chloride was used in the next reaction without further purification.

Synthesis Example 1-1-4

Synthesis of Triphenylsulfonium 2'-(6-Methacryloyloxy-2-oxohexahydro-3,5-methano-2H-cyclopenta[b]furane-7-carbonyloxy)ethanesulfonate (PM-1)

Into a mixed solvent of 40 g $CH_3CN$ and 36 g $H_2O$ were dissolved 16.8 g of sodium 2-hydroxyethanesulfonate (28), 8.2 g of triethylamine, and 0.042 g of 4-dimethylaminopyridine; and then, into this mixture was gradually added at 20° C. or lower the acid chloride (27), obtained by Synthesis Example 1-1-3 and dissolved in 40 g of $CH_3CN$, whereby giving the onium salt (29). After stirred at 25° C. for 2 hours, 40 g of $CH_2Cl_2$ and 166 g of aqueous solution of triphenylsulfonium chloride were added thereinto and the resulting mixture was stirred for 30 minutes. After the organic layer was separated, the aqueous layer was extracted with $CH_2Cl_2$; and the combined organic layer was washed with $H_2O$ for three times. The solvent was removed by distillation under reduced pressure to obtain 22.0 g of the intended product (PM-1) (overall yield of three steps; 51%).

Synthesis Example 1-2

Synthesis of PM-2

Into 300 g of THF and 250 g of $H_2O$ were dissolved 58.8 g of sodium 4-phenolsulfonate and 48.0 g of 25%-aqueous sodium hydroxide; and into this mixture was gradually added at 25° C. a THF solution of 79.9 g of the acid chloride (27) obtained by Synthesis Example 1-1-3. After stirred at 25° C. for 2 hours, 500 g of $CH_2Cl_2$ and 742 g of aqueous solution of triphenylsulfonium chloride were added thereinto, and then the resulting mixture was stirred for 30 minutes. After the organic layer was separated, the aqueous layer was extracted with $CH_2Cl_2$; and the combined organic layer was washed with H₂O for three times. The solvent was removed by distillation under reduced pressure to obtain 119.2 g of the intended product (PM-2) (overall yield of three steps; 58%).

Synthesis Example 1-3

Synthesis of PM-3

By following the procedure similar to that of Synthesis Example 1-1 except that 38.5 g of tert-butyl 6-hydroxy-2-oxo-4-oxahexahydro-3,5-methano-2H-cyclopenta[b]furane-7-carboxylate was used instead of tert-butyl 6-hydroxy-2-oxohexahydro-3,5-methano-2H-cyclopenta[b]furane-7-carboxylate (24) in Synthesis Example 1-1-1 of Synthesis Example 1-1, 34.5 g of triphenylsulfonium 2'-(6-methacryloyloxy-2-oxo-4-oxahexahydro-3,5-methano-2H-cyclopenta[b]furane-7-carbonyloxy)ethanesulfonate (PM-3) was obtained (overall yield of five steps; 36%).

Synthesis Example 1-4

Synthesis of PM-4

By following the procedure similar to that up to Synthesis Example 1-1-3 except that 29.9 g of tert-butyl 6-hydroxy-2-oxo-4-oxahexahydro-3,5-methano-2H-cyclopenta[b]furane-7-carboxylate was used instead of tert-butyl 6-hydroxy-2-oxohexahydro-3,5-methano-2H-cyclopenta[b]furane-7-carboxylate (24) in Synthesis Example 1-1-1 of Synthesis Example 1-1, the acid chloride was obtained. By using this compound and following the procedure similar to that of Synthesis Example 1-2, 32.9 g of triphenylsulfonium 4-(6-methacryloyloxy-2-oxo-4-oxahexahydro-3,5-methano-2H-cyclopenta[b]furane-7-carbonyloxy)benzenesulfonate (PM-4) was obtained (overall yield of five steps; 41%).

Synthesis Example 1-5

Synthesis of PM-5

By following the procedure similar to that of Synthesis Example 1-2 except that 10-phenylphenoxathiinium iodide was used instead of the aqueous solution of triphenylsulfonium chloride in Synthesis Example 1-2, 31.0 g of 10-phenylphenoxathiinium 4'-(6-methacryloyloxy-2-oxohexahydro-3,5-methano-2H-cyclopenta[b]furane-7-carbonyloxy)benzenesulfonate (PM-5) was obtained (overall yield of three steps; 57%).

Synthesis Example 1-6

Synthesis of PM-6

By following the procedure similar to that of Synthesis Example 1-5 except that an aqueous solution of 9-phenyldibenzothiophenium chloride was used instead of 10-phenylphenoxathiinium iodide in Synthesis Example 1-5, 32.0 g of 9-phenyldibenzothiophenium 4'-(6-methacryloyloxy-2-oxohexahydro-3,5-methano-2H-cyclopenta[b]furane-7-carbonyloxy)benzenesulfonate (PM-6) was obtained (overall yield of three steps; 56%).

Synthesis Example 2

Polymers of the present invention were synthesized by the following prescriptions. Composition ratios of respective synthesized polymers are shown in Table 1, and structures of the repeating units are shown in Tables 2 to 5.

Polymer Synthesis Example 2-1

Synthesis of Polymer-1

Into a dropping cylinder were taken under a nitrogen atmosphere 168.8 g of 4-(1-ethoxyethoxystyrene), 15.3 g of acenaphthylene, 16.0 g of triphenylsulfonium 2'-(6-methacryloyloxy-2-oxohexahydro-3,5-methano-2H-cyclopenta[b]furane-7-carbonyloxy)ethanesulfonate (PM-1), 19.4 g of dimethyl 2,2'-azobis(2-methylpropionate) (V-601), and 303 g of methyl ethyl ketone to prepare a monomer solution. Into a different polymerization flask was taken under a nitrogen atmosphere 106 g of methyl ethyl ketone; and after heating it to 80° C. with stirring, the monomer solution was gradually added into it over 4 hours. After the gradual addition, the polymerization solution was stirred for 20 hours with keeping the temperature at 80° C., and then cooled to room temperature. Into the polymerization solution thus obtained were added 100 g of methanol and 1.2 g of oxalic acid and then the resulting mixture was stirred at 40° C. for 5 hours to carry out the deprotection reaction. After neutralized with triethylamine, the reaction solution was concentrated, re-dissolved into 400 g of acetone, and then the mixture was gradually added into 2000 g of H₂O to separate the deposited copolymer by filtration. The copolymer was washed with 400 g of H₂O twice, and then dried at 50° C. under vacuum for 20 hours to obtain a white powdery solid polymer. The obtained polymer was reacted with 31.8 g of (2-methyl-1-propenyl)methyl ether under an acidic condition to obtain Polymer-1 shown below via neutralization, phase-separation, and crystallization processes. The yield was 118 g.

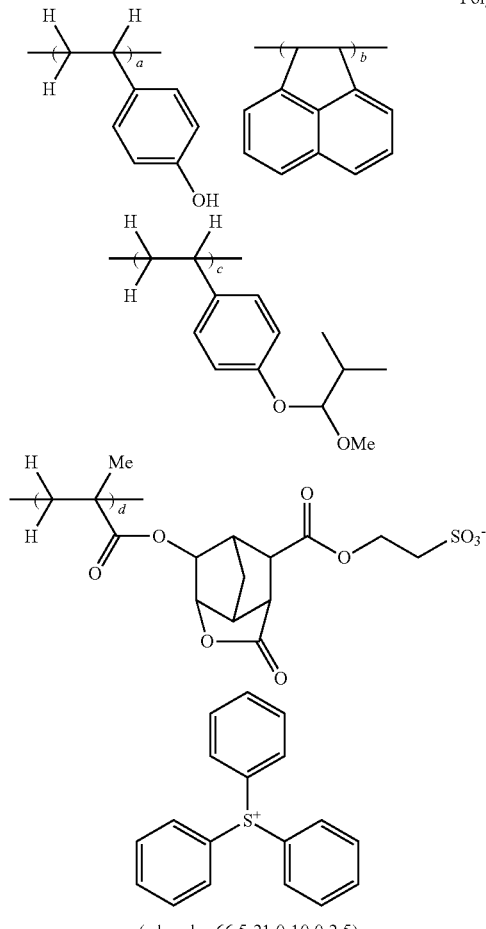

Polymer 1

(a:b:c:d = 66.5:21.0:10.0:2.5)

Polymer Synthesis Example 2-2

Synthesis of Polymer-2

Polymer-2 was obtained by following the procedure similar to that of Polymer Synthesis Example 2-1 except that (2-methyl-1-propenyl)-8-(tricyclo[5,2,1,0$^{2,6}$]decanyl ether was used instead of (2-methyl-1-propenyl)methyl ether in Synthesis Example 2-1.

Polymer Synthesis Example 2-3

Synthesis of Polymer-3

Into a dropping cylinder were taken under a nitrogen atmosphere 166.7 g of 4-hydroxyphenyl methacrylate, 16.3 g of acenaphthylene, 17.0 g of triphenylsulfonium 2'-(6-methacryloyloxy-2-oxohexahydro-3,5-methano-2H-cyclopenta[b]furane-7-carbonyloxy)ethanesulfonate (PM-1), 20.7 g of dimethyl 2,2'-azobis(2-methylpropionate) (V-601), and 303 g of methyl ethyl ketone to prepare a monomer solution. Into a different polymerization flask was taken under a nitrogen atmosphere 106 g of methyl ethyl ketone; and after heating it to 80° C. with stirring, the monomer solution was gradually added into it over 4 hours. After the gradual addition, the polymerization solution was stirred for 4 hours with keeping the temperature at 80° C., and then cooled to room temperature. The polymerization solution thus obtained was gradually added into 4000 g of hexane/diisopropyl ether, and then the deposited copolymer was separated by filtration. The copolymer was washed with 200 g of hexane twice, and then dried at 50° C. under vacuum for 20 hours to obtain a white powdery solid polymer. The obtained polymer was reacted with 33.8 g of (2-methyl-1-propenyl)methyl ether under an acidic condition to obtain Polymer-3 via neutralization, phase-separation, and crystallization processes. The yield was 183 g.

Polymer Synthesis Example 2-4

Synthesis of Polymer-4

Polymer-4 was obtained by following the procedure similar to that of Polymer Synthesis Example 2-3 except that (2-methyl-1-propenyl)-8-(tricyclo[5,2,1,0$^{2,6}$]decanyl ether was used instead of (2-methyl-1-propenyl)methyl ether in Synthesis Example 2-3.

Polymer Syntheses Examples 2-5 to 2-28 and Comparative Polymer Syntheses Examples 2-1 to 2-4

Syntheses of Polymer-5 to Polymer-28 and Comparative Polymer-1 to Comparative Polymer-4

In the case of the polymers having the hydroxystyrene unit, the resins shown in Table 1 were synthesized by following the procedures similar to those of Polymer Synthesis Example 2-1 or 2-2 except that kinds and composition ratios of respective monomers were changed. In the case of the polymers having the 4-hydroxyphenyl methacrylate unit, the resins shown in Table 1 were synthesized by following the procedures similar to those of Polymer Synthesis Example 2-3 or 2-4 except that kinds and composition ratios of the respective monomers were changed.

Polymer Synthesis Example 2-29

Synthesis of Polymer-29

Into a dropping cylinder were taken under a nitrogen atmosphere 44.2 g of 4-hydroxyphenyl methacrylate, 48.3 g of 5-oxo-4-oxatricyclo[4.2.1.0$^{3,7}$]nonane-2-yl methacrylate, 16.0 g of 1-methoxy-2-methyl-1-propyl methacrylate, 41.5 g of triphenylsulfonium 2'-(6-methacryloyloxy-2-oxohexahydro-3,5-methano-2H-cyclopenta[b]furane-7-carbonyloxy)ethanesulfonate (PM-1), 11.1 g of dimethyl 2,2'-azobis(2-methylpropionate) (V-601), and 209 g of methyl ethyl ketone to prepare a monomer solution. Into a different polymerization flask was taken under a nitrogen atmosphere 69.6 g of methyl ethyl ketone; and after heating it to 80° C. with stirring, the monomer solution was gradually added into it over 4 hours. After completion of the gradual addition, the polymerization solution was stirred for 4 hours with keeping the temperature of the solution at 80° C., and then cooled to room temperature. The polymerization solution thus obtained was gradually added into 4000 g of hexane/diisopropyl ether, and then the deposited copolymer was separated by filtration. The copolymer was washed with 200 g of hexane twice, and then dried at 50° C. under vacuum for 20 hours to obtain a white powdery solid polymer.

Polymer Synthesis Example 2-30 and Comparative Polymer Synthesis Example 2-5

Syntheses of Polymer-30 and Comparative Polymer-5

The resins shown in Table 1 were synthesized by following the procedures similar to those of Polymer Synthesis Example 2-29 except that kinds and composition ratios of respective monomers were changed.

Structures of respective units in Table 1 are shown in Tables 2 to 5. Meanwhile, introduction ratios (ratio) in Table 1 are shown by mole ratio.

TABLE 1

| | Unit 1 | ratio (mol %) | Unit 2 | ratio (mol %) | Unit 3 | ratio (mol %) | Unit 4 | ratio (mol %) |
|---|---|---|---|---|---|---|---|---|
| Polymer 1 | PM-1 | 2.5 | A-1 | 66.5 | B-1 | 21.0 | C-1 | 10 |
| Polymer 2 | PM-1 | 2.5 | A-1 | 68.5 | B-3 | 18.0 | C-1 | 11 |
| Polymer 3 | PM-1 | 2.5 | A-2 | 62.0 | B-2 | 25.5 | C-1 | 10 |
| Polymer 4 | PM-1 | 2.5 | A-2 | 65.5 | B-4 | 22.0 | C-1 | 10 |
| Polymer 5 | PM-1 | 3.5 | A-1 | 65.0 | B-1 | 20.5 | C-1 | 11 |
| Polymer 6 | PM-1 | 3.5 | A-1 | 70.5 | B-3 | 17.0 | C-1 | 9 |
| Polymer 7 | PM-1 | 3.5 | A-2 | 62.5 | B-2 | 24.0 | C-1 | 10 |
| Polymer 8 | PM-1 | 3.5 | A-2 | 67.0 | B-4 | 20.5 | C-1 | 9 |
| Polymer 9 | PM-1 | 2.5 | A-1 | 68.5 | B-3 | 18.0 | C-2 | 11 |
| Polymer 10 | PM-1 | 2.5 | A-2 | 65.5 | B-4 | 22.0 | C-2 | 10 |
| Polymer 11 | PM-2 | 2.5 | A-1 | 68.5 | B-1 | 19.0 | C-1 | 10 |
| Polymer 12 | PM-2 | 2.5 | A-1 | 71.5 | B-3 | 16.0 | C-1 | 10 |
| Polymer 13 | PM-2 | 2.5 | A-2 | 63.0 | B-2 | 23.5 | C-1 | 11 |
| Polymer 14 | PM-2 | 2.5 | A-2 | 67.5 | B-4 | 20.0 | C-1 | 10 |
| Polymer 15 | PM-2 | 3.5 | A-1 | 67.0 | B-1 | 18.5 | C-1 | 11 |
| Polymer 16 | PM-2 | 3.5 | A-1 | 71.5 | B-3 | 15.0 | C-1 | 10 |
| Polymer 17 | PM-2 | 3.5 | A-2 | 65.5 | B-2 | 22.0 | C-1 | 9 |
| Polymer 18 | PM-2 | 3.5 | A-2 | 68.0 | B-4 | 18.5 | C-1 | 10 |
| Polymer 19 | PM-2 | 2.5 | A-1 | 70.5 | B-3 | 16.0 | C-2 | 11 |
| Polymer 20 | PM-2 | 2.5 | A-2 | 67.5 | B-4 | 20.0 | C-2 | 10 |
| Polymer 21 | PM-3 | 2.5 | A-1 | 70.0 | B-3 | 17.5 | C-1 | 10 |
| Polymer 22 | PM-3 | 3.5 | A-2 | 66.0 | B-4 | 21.5 | C-1 | 9 |
| Polymer 23 | PM-4 | 2.5 | A-1 | 72.5 | B-3 | 15.0 | C-1 | 10 |
| Polymer 24 | PM-4 | 3.5 | A-2 | 66.5 | B-4 | 19.0 | C-1 | 11 |
| Polymer 25 | PM-5 | 2.5 | A-1 | 72.5 | B-3 | 15.0 | C-1 | 10 |
| Polymer 26 | PM-5 | 3.5 | A-2 | 67.0 | B-4 | 18.5 | C-1 | 11 |

TABLE 1-continued
| | Unit 1 | ratio (mol %) | Unit 2 | ratio (mol %) | Unit 3 | ratio (mol %) | Unit 4 | ratio (mol %) |
|---|---|---|---|---|---|---|---|---|
| Polymer 27 | PM-6 | 2.5 | A-1 | 72.5 | B-3 | 15.0 | C-1 | 10 |
| Polymer 28 | PM-6 | 3.5 | A-2 | 69.0 | B-4 | 18.5 | C-1 | 9 |
| Polymer 29 | PM-1 | 10 | A-2 | 40.0 | B-5 | 15.0 | C-3 | 35 |
| Polymer 30 | PM-1 | 10 | A-2 | 40.0 | B-6 | 15.0 | C-3 | 35 |
| Comparative Polymer 1 | PM-7 | 3.5 | A-1 | 69.5 | B-1 | 17.0 | C-1 | 10 |
| Comparative Polymer 2 | PM-7 | 2.5 | A-1 | 67.0 | B-3 | 20.5 | C-1 | 10 |
| Comparative Polymer 3 | PM-7 | 3.5 | A-2 | 66.5 | B-2 | 21.0 | C-1 | 9 |
| Comparative Polymer 4 | PM-7 | 2.5 | A-2 | 64.0 | B-4 | 23.5 | C-1 | 10 |
| Comparative Polymer 5 | PM-7 | 10 | A-2 | 40.0 | B-5 | 15.0 | C-3 | 35 |
TABLE 2
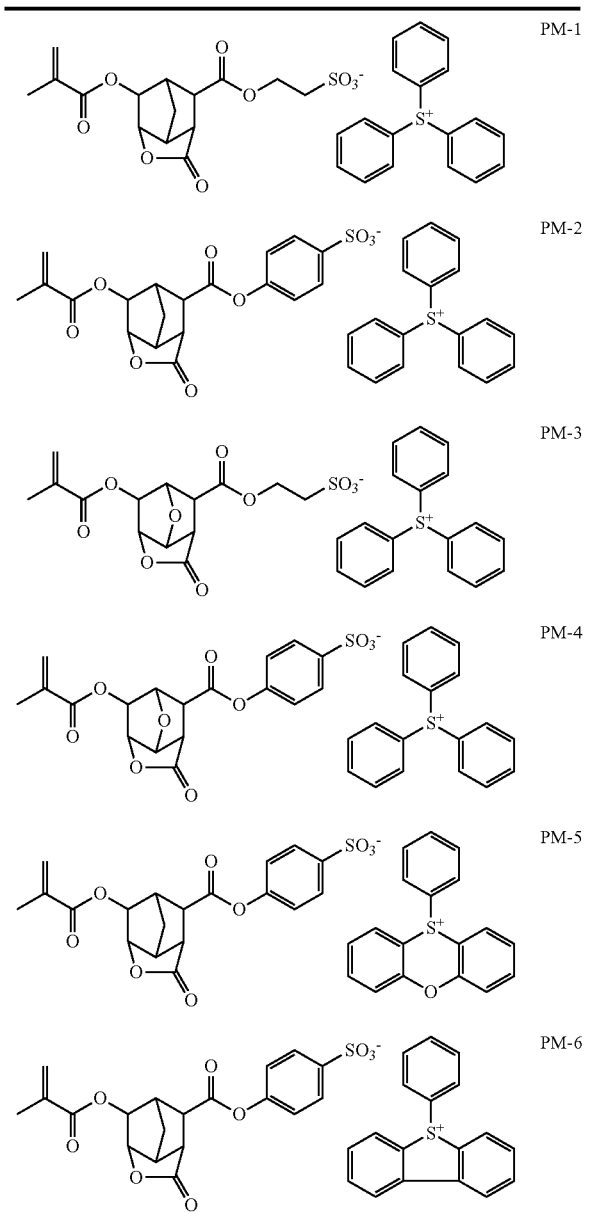
TABLE 2-continued
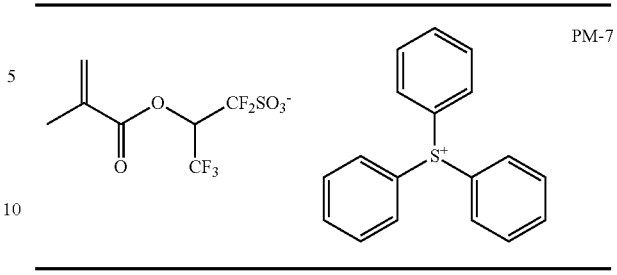
TABLE 3
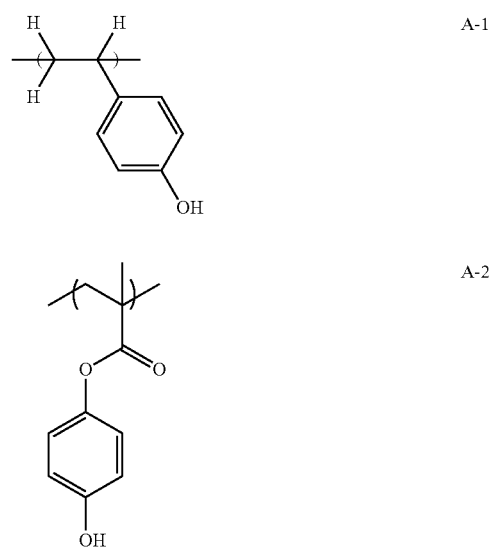
TABLE 4
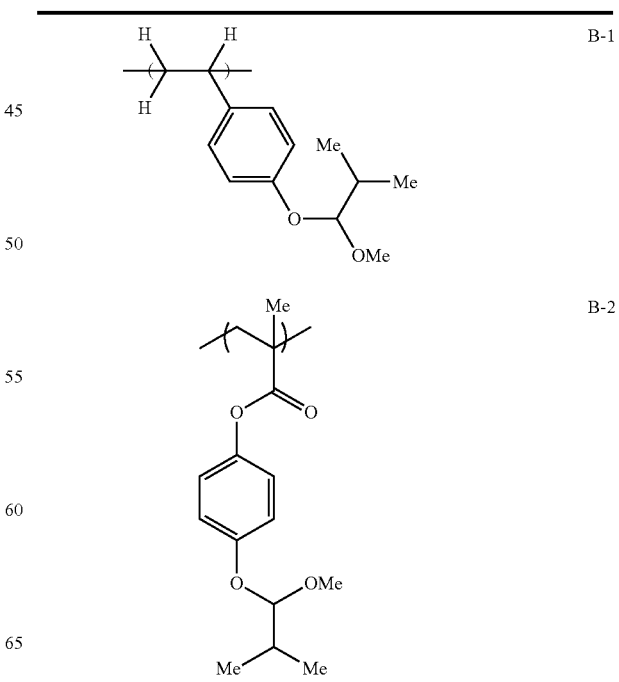

TABLE 4-continued

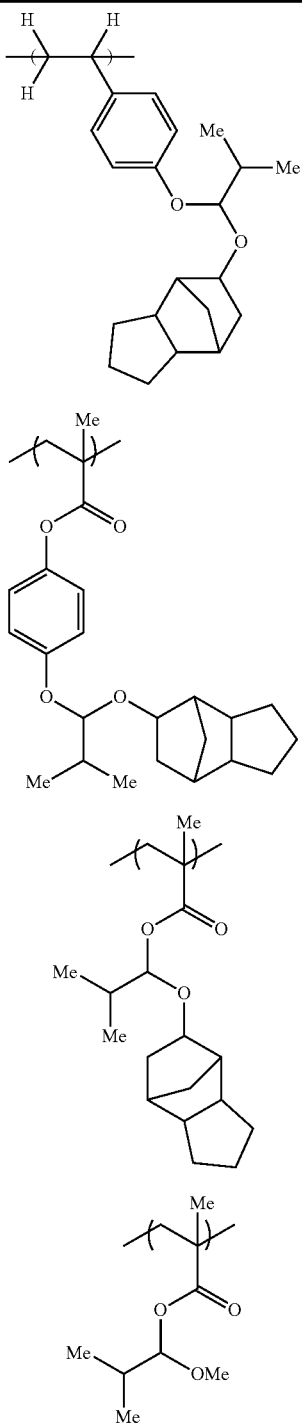

B-3

B-4

B-5

B-6

TABLE 5

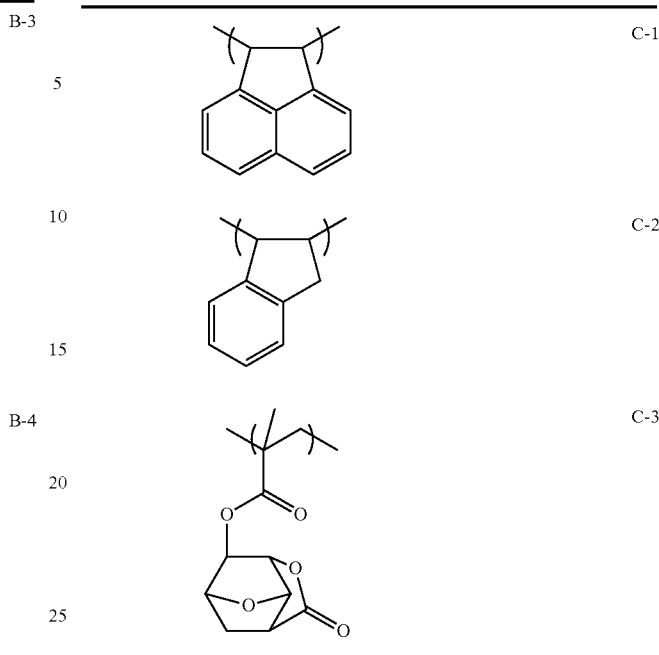

C-1

C-2

C-3

Preparation of Positive Resist Compositions

Each of the polymers synthesized as mentioned above (Polymer-1 to Polymer-30 and Comparative Polymer-1 to Comparative Polymer-5) and the basic compound (Base-1 as shown by the following formula) were dissolved in an organic solvent with the compositions shown in Table 6 to prepare respective resist compositions, which were then filtered through a filter with the size of 0.2 μm, or through a nylon or UPE filter with the size of 0.02 μm to obtain respective positive resist composition solutions.

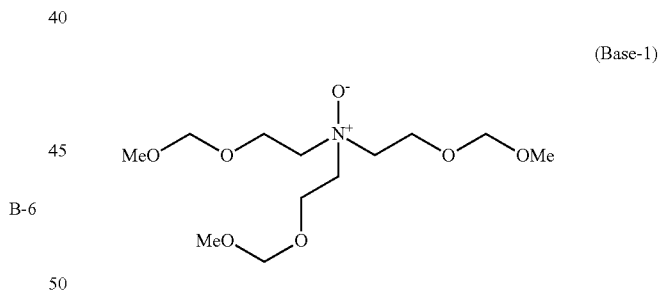

(Base-1)

The organic solvents shown in Table 6 are PGMEA (propylene glycol monomethyl ether acetate), EL (ethyl lactate), PGME (propylene glycol monomethyl ether), and CyH (cyclohexanone). Into each solution, 0.075 part by mass of PF-636 (manufactured by OMNOVA SOLUTIONS, Inc.) was added as a surfactant.

TABLE 6

| | Polymer | Basic Compound | Solvent 1 | Solvent 2 | Solvent 3 |
|---|---|---|---|---|---|
| Example 1 | Polymer 1 (80) | Base-1 | PGMEA (1,000) | EL (1,000) | PGME (1,000) |
| Example 2 | Polymer 2 (80) | Base-1 | PGMEA (1,000) | EL (1,000) | PGME (1,000) |
| Example 3 | Polymer 3 (80) | Base-1 | PGMEA (1,000) | EL (1,000) | PGME (1,000) |
| Example 4 | Polymer 4 (80) | Base-1 | PGMEA (1,000) | EL (1,000) | PGME (1,000) |
| Example 5 | Polymer 5 (80) | Base-1 | PGMEA (1,000) | EL (1,000) | PGME (1,000) |

TABLE 6-continued

| | Polymer | Basic Compound | Solvent 1 | Solvent 2 | Solvent 3 |
|---|---|---|---|---|---|
| Example 6 | Polymer 6 (80) | Base-1 | PGMEA (1,000) | EL (1,000) | PGME (1,000) |
| Example 7 | Polymer 7 (80) | Base-1 | PGMEA (1,000) | EL (1,000) | PGME (1,000) |
| Example 8 | Polymer 8 (80) | Base-1 | PGMEA (1,000) | EL (1,000) | PGME (1,000) |
| Example 9 | Polymer 9 (80) | Base-1 | PGMEA (1,000) | EL (1,000) | PGME (1,000) |
| Example 10 | Polymer 10 (80) | Base-1 | PGMEA (1,000) | EL (1,000) | PGME (1,000) |
| Example 11 | Polymer 11 (80) | Base-1 | PGMEA (1,000) | EL (1,000) | PGME (1,000) |
| Example 12 | Polymer 12 (80) | Base-1 | PGMEA (1,000) | EL (1,000) | PGME (1,000) |
| Example 13 | Polymer 13 (80) | Base-1 | PGMEA (1,000) | EL (1,000) | PGME (1,000) |
| Example 14 | Polymer 14 (80) | Base-1 | PGMEA (1,000) | EL (1,000) | PGME (1,000) |
| Example 15 | Polymer 15 (80) | Base-1 | PGMEA (1,000) | EL (1,000) | PGME (1,000) |
| Example 16 | Polymer 16 (80) | Base-1 | PGMEA (1,000) | EL (1,000) | PGME (1,000) |
| Example 17 | Polymer 17 (80) | Base-1 | PGMEA (1,000) | EL (1,000) | PGME (1,000) |
| Example 18 | Polymer 18 (80) | Base-1 | PGMEA (1,000) | EL (1,000) | PGME (1,000) |
| Example 19 | Polymer 19 (80) | Base-1 | PGMEA (1,000) | EL (1,000) | PGME (1,000) |
| Example 20 | Polymer 20 (80) | Base-1 | PGMEA (1,000) | EL (1,000) | PGME (1,000) |
| Example 21 | Polymer 21 (80) | Base-1 | PGMEA (1,000) | EL (1,000) | PGME (1,000) |
| Example 22 | Polymer 22 (80) | Base-1 | PGMEA (1,000) | EL (1,000) | PGME (1,000) |
| Example 23 | Polymer 23 (80) | Base-1 | PGMEA (1,000) | EL (1,000) | PGME (1,000) |
| Example 24 | Polymer 24 (80) | Base-1 | PGMEA (1,000) | EL (1,000) | PGME (1,000) |
| Example 25 | Polymer 25 (80) | Base-1 | PGMEA (1,000) | EL (1,000) | PGME (1,000) |
| Example 26 | Polymer 26 (80) | Base-1 | PGMEA (1,000) | EL (1,000) | PGME (1,000) |
| Example 27 | Polymer 27 (80) | Base-1 | PGMEA (1,000) | EL (1,000) | PGME (1,000) |
| Example 28 | Polymer 28 (80) | Base-1 | PGMEA (1,000) | EL (1,000) | PGME (1,000) |
| Example 29 | Polymer 29 (80) | Base-1 | PGMEA (800) | CyH (1,600) | PGME (400) |
| Example 30 | Polymer 30 (80) | Base-1 | PGMEA (800) | CyH (1,600) | PGME (400) |
| Com. Ex. 1 | Comparative 1 (80) polymer | Base-1 | PGMEA (1,000) | EL (1,000) | PGME (1,000) |
| Com. Ex. 2 | Comparative 2 (80) polymer | Base-1 | PGMEA (1,000) | EL (1,000) | PGME (1,000) |
| Com. Ex. 3 | Comparative 3 (80) polymer | Base-1 | PGMEA (1,000) | EL (1,000) | PGME (1,000) |
| Com. Ex. 4 | Comparative 4 (80) polymer | Base-1 | PGMEA (1,000) | EL (1,000) | PGME (1,000) |
| Com. Ex. 5 | Comparative 5 (80) polymer | Base-1 | PGMEA (800) | CyH (1,600) | PGME (400) |

Evaluation of Electron Beam Drawing

Examples 1 to 28 and Comparative Examples 1 to 4

The positive resist composition prepared as mentioned above (Examples 1 to 28 and Comparative Examples 1 to 4) was applied by spin coating onto a mask blank with the size of 152-mm square having a chromium oxynitride film on its outermost surface (ACT-M, manufactured by Tokyo Electron, Ltd.), and then it was pre-baked on a hot plate at 100° C. for 600 seconds to obtain a resist film having a film thickness of 60 nm. Film thickness of the obtained resist film was measured by using an optical measurement instrument (NanoSpec; manufactured by Nanometrics, Inc.). The measurement was made at 81 spots on surface of a blank substrate except for an outer edge part within 10 mm inside from the blank peripheral; and then the average film thickness and range of the film thickness were calculated.

Photo-exposure was made with an electron beam exposure instrument (EBM-5000plus, manufactured by NuFlare Technology, Inc. with acceleration voltage of 50 keV), baking (PEB: post exposure bake) was done at 100° C. for 600 seconds, and then development was made with an aqueous tetramethyl ammonium hydroxide solution with concentration of 2.38% by mass to obtain a positive resist pattern. The obtained resist pattern was evaluated as following.

The patterned mask blank thus obtained was observed with a SEM (scanning electron microscope) to measure the edge roughness of 100 nmLS by taking the exposure dose to resolve the 1:1 line-and-space with 200 nm at 1:1 as the optimum exposure dose ($\mu C/cm^2$) and the minimum size obtained with the exposure dose to resolve the line-and-space with 200 nm at 1:1 as the resolution (critical resolution power). Pattern profile was judged whether it was rectangular or not with visual observation. Adhesion was judged as to peeling-off with hovering visual observation by the SEM. Evaluation results of the resist compositions of the present invention and of Comparative Examples by the EB drawing are shown in Table 7.

TABLE 7

| | Optimum exposure dose ($\mu C/cm^2$) | Critical Resolusion Power (nm) | LER (nm) | Pattern Profile | Adhesion |
|---|---|---|---|---|---|
| Example 1 | 24 | 40 | 6.0 | Rectangular | Good |
| Example 2 | 25 | 35 | 6.1 | Rectangular | Good |
| Example 3 | 27 | 40 | 6.4 | Rectangular | Good |
| Example 4 | 26 | 40 | 5.9 | Rectangular | Good |
| Example 5 | 28 | 35 | 6.2 | Rectangular | Good |
| Example 6 | 26 | 35 | 6.4 | Rectangular | Good |
| Example 7 | 25 | 40 | 6.0 | Rectangular | Good |
| Example 8 | 27 | 40 | 5.9 | Rectangular | Good |
| Example 9 | 28 | 45 | 6.9 | Rectangular | Good |
| Example 10 | 27 | 45 | 6.8 | Rectangular | Good |
| Example 11 | 26 | 40 | 6.1 | Rectangular | Good |
| Example 12 | 25 | 35 | 6.2 | Rectangular | Good |
| Example 13 | 28 | 40 | 6.5 | Rectangular | Good |
| Example 14 | 29 | 40 | 6.4 | Rectangular | Good |
| Example 15 | 24 | 35 | 6.3 | Rectangular | Good |
| Example 16 | 27 | 40 | 6.2 | Rectangular | Good |
| Example 17 | 26 | 40 | 6.4 | Rectangular | Good |
| Example 18 | 28 | 40 | 6.3 | Rectangular | Good |
| Example 19 | 29 | 45 | 6.7 | Rectangular | Good |
| Example 20 | 25 | 45 | 6.6 | Rectangular | Good |
| Example 21 | 26 | 40 | 6.4 | Rectangular | Good |
| Example 22 | 27 | 35 | 6.1 | Rectangular | Good |

TABLE 7-continued

| | Optimum exposure dose ($\mu C/cm^2$) | Critical Resolution Power (nm) | LER (nm) | Pattern Profile | Adhesion |
|---|---|---|---|---|---|
| Example 23 | 26 | 40 | 6.3 | Rectangular | Good |
| Example 24 | 28 | 40 | 6.4 | Rectangular | Good |
| Example 25 | 25 | 40 | 6.5 | Rectangular | Good |
| Example 26 | 27 | 35 | 6.2 | Rectangular | Good |
| Example 27 | 25 | 40 | 6.3 | Rectangular | Good |
| Example 28 | 26 | 35 | 6.4 | Rectangular | Good |
| Comparative Example 1 | 28 | 90 | 9.5 | Negative Profile | Pattern-Peeling off |
| Comparative Example 2 | 25 | 120 | 9.8 | Negative Profile | Pattern-Peeling off |
| Comparative Example 3 | 29 | 100 | 10.2 | Negative Profile | Pattern-Peeling off |
| Comparative Example 4 | 27 | 120 | 9.9 | Negative Profile | Pattern-Peeling off |

Evaluation of EUV Exposure

Examples 29 to 30 and Comparative Example 5

The positive resist composition prepared as mentioned above (Examples 29 to 30 and Comparative Example 5) was applied by spin coating on a Si substrate having the size of 4-inch diameter treated with hexamethyl disilazane (HMDS) vapor primer, and then it was pre-baked on a hot plate at 105° C. for 60 seconds to prepare the resist film with a thickness of 50 nm. This was exposed to EUV by a dipole illumination with NA of 0.3.

Immediately after the exposure, post exposure baking (PEB) was done on a hot plate for 60 seconds, and then puddle development was made with an aqueous tetramethyl ammonium hydroxide (TMAH) solution with concentration of 2.38% by mass for 30 seconds to obtain a positive resist pattern.

The resist pattern thus obtained was evaluated as following. The edge roughness (LER) of 35 nmLS was measure with an SEM by taking the minimum size obtained with the exposure dose to resolve the line-and-space with 35 nm at 1:1 as the resolution (critical resolution power). Pattern profile was judged whether it was rectangular or not with visual observation. Adhesion was judged as to peeling-off with hovering visual observation by the SEM. Evaluation results of the resist compositions of the present invention and of Comparative Example by the EUV drawing are shown in Table 8.

TABLE 8

| | Optimum exposure dose ($mJ/cm^2$) | Critical Resolution Power (nm) | LER (nm) | Pattern Profile | Adhesion |
|---|---|---|---|---|---|
| Example 29 | 15 | 28 | 4.0 | Rectangular | Good |
| Example 30 | 14 | 26 | 4.1 | Rectangular | Good |
| Comparative Example 5 | 12 | 70 | 9.6 | Negative Profile | Pattern-Peeling off |

The results shown in Tables 7 and 8 will be explained. Any of the resist compositions using the polymer having the units shown by the general formulae (2) and (3) (Examples 1 to 28 or Examples 29 and 30) showed good resolution and line edge roughness values. They showed the rectangular pattern profile and good adhesion with the substrate. On the other hand, in Comparative Examples 1 to 4 or Comparative Example 5, in which a resist composition using a polymer having a repeating unit capable of generating a fluorinated alkanesulfonic acid by photo-exposure is used, a pattern profile thereof was poor, and in addition, phenomenon of peel-off of the pattern from the substrate was confirmed. Because of these phenomena, poorer resolution and line edge roughness as compared with Examples were resulted. These may be caused by the decreased adhesion with the substrate because the fluorine atom contained in the unit that generates the fluorinated alkanesulfonic acid has a water-repellent property.

As can be seen clearly in the above explanation, the resist composition of the present invention can give a resist film having excellent adhesion with a substrate, and in addition, can form a pattern with a small line edge roughness by photo-exposure. The patterning process using this is useful for a photolithography in semiconductor manufacturing, especially in processing of a photomask blanks.

It must be noted here that the present invention is not limited to the embodiments as described above. The foregoing embodiments are mere examples; any form having substantially the same composition as the technical concept described in claims of the present invention and showing similar effects is included in the technical scope of the present invention.

What is claimed is:
1. A sulfonium salt shown by the following general formula (1),

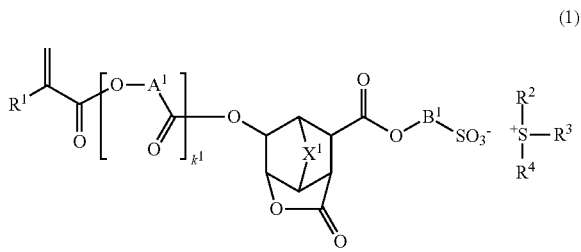

wherein
$R^1$ represents any of a hydrogen atom, a fluorine atom, a methyl group, and a trifluoromethyl group,
each $R^2$, $R^3$, and $R^4$ independently represents any of a substituted or unsubstituted linear, branched, or cyclic alkyl group, alkenyl group, and oxoalkyl group having 1 to 10 carbon atoms; any of a substituted or unsubstituted aryl, aralkyl, and aryl oxoalkyl group having 6 to 18 carbon atoms; or any two or more of $R^2$, $R^3$, and $R^4$ may be bonded with each other to form a ring together with a sulfur atom in the formula,
$X^1$ represents O or $CH_2$,
$A^1$ represents a linear, a branched, or a cyclic divalent hydrocarbon group having 1 to 10 carbon atoms,
$B^1$ represents an alkylene group having 1 to 10 carbon atoms or an arylene group having 6 to 18 carbon atoms wherein these groups may contain an ether oxygen atom, and
$k^1$ represents an integer of 0 or 1.
2. A polymer having a repeating unit shown by the following general formula (2) and a repeating unit shown by the following general formula (3),

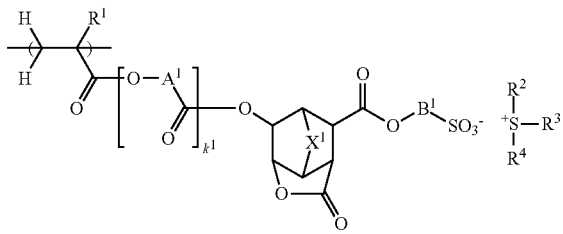

(2)

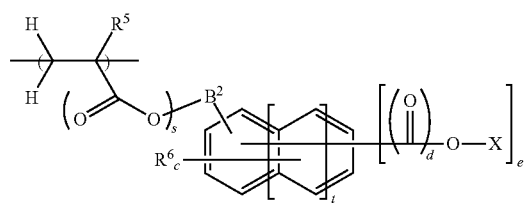

(4)

wherein

R¹ represents any of a hydrogen atom, a fluorine atom, a methyl group, and a trifluoromethyl group, each R², R³, and R⁴ independently represents any of a substituted or unsubstituted linear, branched, or cyclic alkyl group, alkenyl group, and oxoalkyl group having 1 to 10 carbon atoms; any of a substituted or unsubstituted aryl, aralkyl, and aryl oxoalkyl group having 6 to 18 carbon atoms; or any two or more of R², R³, and R¹ may be bonded with each other to form a ring together with a sulfur atom in the formula, X¹ represents O or $CH_2$, A¹ represents a linear, a branched, or a cyclic divalent hydrocarbon group having 1 to 10 carbon atoms, B¹ represents an alkylene group having 1 to 10 carbon atoms or an arylene group having 6 to 18 carbon atoms wherein these groups may contain an ether oxygen atom, and k¹ represents an integer of 0 or 1; and

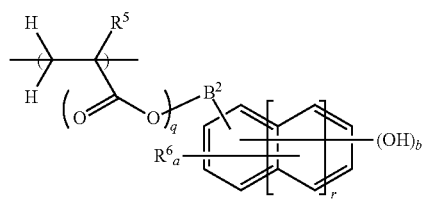

(3)

wherein

"q" represents 0 or 1,

"r" represents an integer of 0 to 2,

R⁵ represents any of a hydrogen atom, a fluorine atom, a methyl group, and a trifluoromethyl group, each R⁶ independently represents a hydrogen atom or an alkyl group having 1 to 6 carbon atoms, B² represents a single bond or an alkylene group having 1 to 10 carbon atoms and optionally containing an ether bond, "a" represents an integer satisfying $a \leq 5+2r-b$, and "b" represents an integer of 1 to 3.

3. The polymer according to claim 2, wherein the polymer contains further a repeating unit shown by the following general formula (4) as the unit to make the polymer alkaline-soluble by the action of an acid that is protected by an acid-labile group, wherein "s" represents 0 or 1, "t" represents an integer of 0 to 2, R⁵ and R⁶ represent the same meanings as before, B³ represents a single bond or an alkylene group having 1 to 10 carbon atoms and optionally containing an ether bond, "c" represents an integer satisfying $c \leq 5+2t-e$, "d" represents 0 or 1, "e" represents an integer of 1 to 3, and X represents an acid-labile group when "e" is 1; and a hydrogen atom or an acid-labile group when "e" is 2 or more, while at least one of X is an acid-labile group.

4. The polymer according to claim 2, wherein the polymer contains further a repeating unit shown by the following general formulae (5) and/or (6),

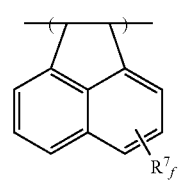

(5)

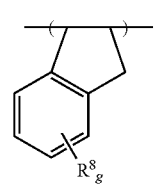

(6)

wherein

"f" represents an integer of 0 to 6, each R⁷ independently represents any of a hydrogen atom, an alkyl group or a primary or a secondary alkoxy group having 1 to 6 carbon atoms and optionally substituted with a halogen atom, and an alkylcarbonyloxy group having 1 to 7 carbon atoms and optionally substituted with a halogen atom, "g" represents an integer of 0 to 4, and each R⁸ independently represents any of a hydrogen atom, an alkyl group or a primary or a secondary alkoxy group having 1 to 6 carbon atoms and optionally substituted with a halogen atom, and an alkylcarbonyloxy group having 1 to 7 carbon atoms and optionally substituted with a halogen atom.

5. The polymer according to claim 3, wherein the polymer contains further a repeating unit shown by the following general formulae (5) and/or (6),

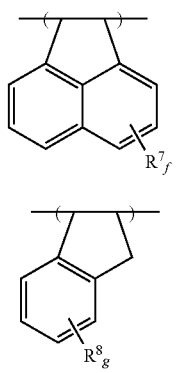

wherein
"f" represents an integer of 0 to 6,
each $R^7$ independently represents any of a hydrogen atom, an alkyl group or a primary or a secondary alkoxy group having 1 to 6 carbon atoms and optionally substituted with a halogen atom, and an alkylcarbonyloxy group having 1 to 7 carbon atoms and optionally substituted with a halogen atom,
"g" represents an integer of 0 to 4, and
each $R^8$ independently represents any of a hydrogen atom, an alkyl group or a primary or a secondary alkoxy group having 1 to 6 carbon atoms and optionally substituted with a halogen atom, and an alkylcarbonyloxy group having 1 to 7 carbon atoms and optionally substituted with a halogen atom.

6. A chemically amplified resist composition wherein the polymer according to claim 2 is contained therein as a base polymer.

7. A chemically amplified resist composition wherein the polymer according to claim 3 is contained therein as a base polymer.

8. A chemically amplified resist composition wherein the polymer according to claim 4 is contained therein as a base polymer.

9. A chemically amplified resist composition wherein the polymer according to claim 5 is contained therein as a base polymer.

10. A resist patterning process wherein the process comprises a step of forming a resist film on a substrate to be processed by using the chemically amplified resist composition according to claim 6, a step of pattern-exposure to a high energy beam, and a step of obtaining a resist pattern by developing with an alkaline developer.

11. A resist patterning process wherein the process comprises a step of forming a resist film on a substrate to be processed by using the chemically amplified resist composition according to claim 7, a step of pattern-exposure to a high energy beam, and a step of obtaining a resist pattern by developing with an alkaline developer.

12. A resist patterning process wherein the process comprises a step of forming a resist film on a substrate to be processed by using the chemically amplified resist composition according to claim 8, a step of pattern-exposure to a high energy beam, and a step of obtaining a resist pattern by developing with an alkaline developer.

13. A resist patterning process wherein the process comprises a step of forming a resist film on a substrate to be processed by using the chemically amplified resist composition according to claim 9, a step of pattern-exposure to a high energy beam, and a step of obtaining a resist pattern by developing with an alkaline developer.

14. The resist patterning process according to claim 10, wherein an EUV or an electron beam is used as the high energy beam.

15. The resist patterning process according to claim 11, wherein an EUV or an electron beam is used as the high energy beam.

16. The resist patterning process according to claim 12, wherein an EUV or an electron beam is used as the high energy beam.

17. The resist patterning process according to claim 13, wherein an EUV or an electron beam is used as the high energy beam.

18. The resist patterning process according to claim 10, wherein the substrate to be processed comprises a chromium-containing material in its outermost surface.

19. The resist patterning process according to claim 11, wherein the substrate to be processed comprises a chromium-containing material in its outermost surface.

20. The resist patterning process according to claim 12, wherein the substrate to be processed comprises a chromium-containing material in its outermost surface.

21. The resist patterning process according to claim 13, wherein the substrate to be processed comprises a chromium-containing material in its outermost surface.

22. The resist patterning process according to claim 14, wherein the substrate to be processed comprises a chromium-containing material in its outermost surface.

23. The resist patterning process according to claim 15, wherein the substrate to be processed comprises a chromium-containing material in its outermost surface.

24. The resist patterning process according to claim 16, wherein the substrate to be processed comprises a chromium-containing material in its outermost surface.

25. The resist patterning process according to claim 17, wherein the substrate to be processed comprises a chromium-containing material in its outermost surface.

26. The resist patterning process according to claim 10, wherein a photomask blank is used as the substrate to be processed.

27. The resist patterning process according to claim 14, wherein a photomask blank is used as the substrate to be processed.

28. The resist patterning process according to claim 18, wherein a photomask blank is used as the substrate to be processed.

* * * * *